(12) United States Patent
Zamoyski

(10) Patent No.: US 8,197,858 B2
(45) Date of Patent: Jun. 12, 2012

(54) BONE MICROENVIRONMENT MODULATED SEIZURE TREATMENTS

(76) Inventor: Mark John Zamoyski, San Jose, CA (US)

( * ) Notice: Subject to any disclaimer, the term of this patent is extended or adjusted under 35 U.S.C. 154(b) by 542 days.

(21) Appl. No.: 12/322,764

(22) Filed: Feb. 6, 2009

(65) Prior Publication Data
US 2010/0203168 A1 Aug. 12, 2010

(51) Int. Cl.
*A61K 33/06* (2006.01)
*A61K 31/56* (2006.01)
*A61K 38/23* (2006.01)
*A61K 33/42* (2006.01)
*A61K 39/395* (2006.01)
*A61K 31/565* (2006.01)

(52) U.S. Cl. ..... 424/682; 424/685; 424/601; 424/133.1; 514/178; 514/12; 514/182

(58) Field of Classification Search .......... None
See application file for complete search history.

(56) References Cited

U.S. PATENT DOCUMENTS

| | | | | |
|---|---|---|---|---|
| 5,441,933 | A * | 8/1995 | Lattanzi et al. | 514/11.9 |
| 5,811,120 | A * | 9/1998 | Gibson et al. | 424/464 |
| 6,228,849 | B1 | 5/2001 | Thys-Jacobs | |
| 2007/0269539 | A1* | 11/2007 | Marshall et al. | 424/752 |

OTHER PUBLICATIONS

"Definition of including": Morris, William "The American Heritage Dictionary", 2nd College Edition, Boston, Houghton Mifflin Company, 1982.*
Borowicz et al., "Influence of sexual hormone antagonists on the anticonvulsant action of conventional antiepileptic drugs against electrically- and pentylenetetrazol-induced seizures in mice", European Neuropsychopharmacology, 14, (2004), 77-85.*
Scharfman et al., "A rat model of epilepsy in women: a tool to study physiological interactions between endocrine systems and seizures", Endocrinology, Sep. 2009, 150(9), 4437-4442.*
Dodick and Gargus, "Why Migraines Strike", Scientific American, Aug. 2008, p. 58.
Moline and Zendell, "Evaluating and Managing Premenstrual Syndrome", 2000, Medscape.
Martin V T MD and Michael Behbehani, PhD, "Ovarian Hormones and Migraine Headache: Understanding Mechanisms and Pathogenesis—Part I", © 2006 Blackwell Publishing, Medscape.
Rosen C J, "Restoring Aging Bones", Scientific American, Mar. 2003.
Biochemical Pathways, edited by Gerhard Michal, Wiley & Sons, 1999, p. 205, Figure 17.1-6.
Molecular Biology of the Cell, Garland Publishing, third edition, p. 508, p. 536.
Nachshen D A, "Regulation of cytosolic calcium concentration in presynaptic nerve endings . . . " J. Physiol. Jun. 1985; 363: 87-101, Fig. 1B on p. 90.

(Continued)

*Primary Examiner* — Ernst Arnold
*Assistant Examiner* — Hong Yu

(57) ABSTRACT

Novel etiology underlying certain types of seizures and migraines is presented, whereby changes in endocrine levels result in changes in osteoclast activity levels which in turn result in elevated extracellular Ca2+ levels which in turn result in systemic alterations in nerves muscles, including increased nerve membrane depolarization, enhanced calcium channel mediated neurotransmitter release, and increased muscle contractility via sarcoplasmic reticulum calcium release channel mediated tropomyosin block removal, which in turn result in increased seizure risk in people with low seizure thresholds. Treatment methods are provided that modulate the bone microenvironment to provide an etiology based seizure treatment method that simultaneously reduces nerve sensitivity and muscle contractility. Preferred embodiments include use of SERMs such as raloxifene, testosterone, estrogen, calcimimetics such as cinacalcet, RANKL inhibitors such as denosumab, and bisphosphonate such as risedronate.

1 Claim, 3 Drawing Sheets

Map of Sensory Nerves to Somatosensory Cortex

OTHER PUBLICATIONS

Neuroscience in Medicine, Humana Press, Second Edition, p. 472.
Clayton A H MD, "Menstrual Migraine", Primary Psychiatry, 2006.
Macdonald R L, Cerebral Vasospasm, Thieme, 2005, p. 43, p. 44.
Therapy of Renal Diseases and Related Disorders, Second Edition, Kluwer Academic Publishers, 1991, p. 98.
Miyaura et. al., ". . . Prostaglandin E2-mediated Bone Resorption Associated with Inflammation", J. Exp. Med., vol. 197, No. 10, May 19, 2003 1303-1310.
Witte F, "The Madness of Migraine", Scientific American Mind, Dec. 2006/ Jan. 2007, pp. 39-43.
"Migraines and Serotonin Receptors", Society for Neuroscience, Feb. 1998.
Durham P L, "CGRP-Receptor Antagonists—A Fresh Approach to Migraine Therapy?", New England Journal of Medicine 350;11, Mar. 11, 2004.
Wang and Lambert, "GABAB Receptors Couple to Potassium and Calcium Channels . . . " Journal of Neurophysiology, vol. 83, No. 2. Feb. 2000, pp. 1073-1078.
Epilepsy Foundation Website, http://www.epilepsyfoundation.org.
WebMD, Epilepsy Health Center Reference collaboration with Cleveland Clinic, "Epilepsy: Medications to Treat Seizures", website printout of Jul. 13, 2008.
Electroencephalography, Niedermeyer and Da Silva, p. 444-445.
Edmondson J W et. al., "Tetany:quantitative interrelationships between calcium and alkalosis", Am. J. Physiol, Apr. 1975; 228(4):1082-6.
Science Daily, Jul. 1, 2008 synopsis of Vanderbilt University study conducted by Dr. Alfred George.
Short R, "Effect of anti epileptic drugs on bone density in ambulatory patients", Neurology 2002;58:1348-1350.
Elliott J et. al., "Osteoprotective Knowledge in a Multiethnic Epilepsy Population", J. Neurosci. Nurs., 2008;40(1):14-24).
Brodie M J et. al. "Efficacy and safety of Remacemide versus Carbamazepine . . . ", Epilepsy & Behavior, vol. 3, No. 2, Apr. 2002, pp. 140-146.
Mintzer S et. al., "Vitamin D levels and Bone Turnover in Epilepsy Patients Taking Carbamazepine or Oxcarbazepine", Epilepsia, 47(3):510-515, 2006.
Duncan S et. al., "How common is catamenial epilepsy", Epilepsia, Sep.-Oct. 1993; 34(5):827-31.
Ginsburg et. al., "Half life of Estradiol in Postmenopausal Women", Gynecologic and Obstetric Investigation, 1998;45:45-48.
Harrison's Principles of Internal Medicine, McGraw-Hill, 15th edition, p. 2146-2147.
Androderm Testosterone Transdermal Delivery System, Full Prescribing Information, WatsonPharma, Nov. 2005.
Fortical (Calcitonin-Salmon) Nasal Spray, Full Prescribing Information, Upsher-Smith, Jun. 2006.
Sensipar, (Cinacalcet), Full Prescribing Information, Amgen, May 2008.
Denosumab, (RANK Ligand antibody), Amgen, Jul. 25, 2008 press release.
Actonel (risedronate tablets), Full Prescribing Information, Procter & Gamble Pharmaceuticals.
Evista (raloxifene tablets), Full Prescribing Information, Eli Lilly, 2003.

* cited by examiner

BONE MICROENVIRONMENT MODULATED SEIZURE TREATMENTS

CROSS REFERENCE TO RELATED APPLICATIONS

The application is related to application Ser. No. 11/975,465 filed on Oct. 19, 2007 for bone microenvironment modulated migraine treatments. Application Ser. No. 11/975,465 disclosed novel etiology underlying certain types of headaches and migraines, whereby changes in endocrine levels resulted in changes in osteoclast activity which in turn resulted in elevated extracellular Ca2+ levels which in turn resulted in systemic alterations in neurological and muscular function that manifested as headaches and migraines. Instant application expands the scope of the original application to seizures and provides examples of how to modulate the bone microenvironment to prevent such seizures.

STATEMENT REGARDING FEDERALLY SPONSORED RESEARCH

Not Applicable.

INCORPORATION-BY-REFERENCE OF MATERIAL SUBMITTED ON A CD

Not Applicable.

BACKGROUND OF THE INVENTION

1. Field of the Invention

The invention relates to compositions and methods for the treatment of seizures and migraines.

2. Description of Related Art

The etiology of headaches, migraines, and most seizures has eluded prior art researchers. The novel etiology/pathogenesis provided in instant application ties all three together to a common underlying etiology. Novel etiology/pathogenesis based treatment methods for seizures and migraines are disclosed, versus prior art's symptom/observation based treatment methods.

Many prior art theories have been proposed, related to both migraines and seizures, however none have been able to account for all of the observed symptoms and diagnostic test results. Instant application provides a novel etiology and underlying pathogenesis which accounts for the disparate observations.

In summary, present invention discloses that oscillations in endocrine levels (e.g. estrogen, testosterone, prostaglandins, the active form of vitamin D, and others) alter the bone micro environment (i.e. osteoclast and/or osteoblast activity) in a manner the results in release of calcium ($Ca^{2+}$) from the bone into the extracellular fluid, which in turn alters the nerve micro environment (via nerve membrane depolarization, enhanced neurotransmitter release at the synapse, and post tetanic potentiation) and alters the muscular micro environment (via enhanced neurotransmitter release at the neuromuscular junction and via enhanced muscular contractility). Any of the underlying endocrine oscillations mentioned above will result in the same pathogenesis and often multiple endocrine oscillations can occur simultaneously, contributing to the severity of the resulting migraine or seizure.

In contrast, prior art theories are based on localized observations, and as such cannot adequately explain the full spectrum of observed effects. Many different prior art theories exist.

Because it is estimated that two thirds of the world's 300 million migraine sufferers are women aged 15 to 55, suggesting estrogen plays a role, (Dodick and Gargus, "*Why Migraines Strike*", *Scientific American*, August 2008, p. 58) a large part of the migraine discussion in this application is focused on comparing the novel pathogenesis presented under present invention to the large body or prior art work done on menstrual cycle related migraines. However, the same pathogenesis applies to seizures in people with low seizure thresholds as well as the same pathogenesis occurs in other endocrine—bone microenvironment mediated seizures and migraines.

Premenstrual Headaches: For purposes of present invention, premenstrual headaches are meant to loosely refer to the following set of symptoms, as described by one sufferer. The headache starts the day before the start of menstrual bleeding and lasts until the start of menstrual bleeding. The headache first manifests as a low level headache and ramps up over several hours into persistent, intense pain that in not at the very back or very front of the head and is accompanied by a hypersensitivity to sound. The headache may be accompanied by nausea and irritability. The sufferer prefers a dark, quiet room and going to sleep, as the headache is gone by the next morning at the start of menstruation.

Premenstrual Migraines: Premenstrual migraines are pulsating in nature, are often one sided, and may be more focused toward the front of the head. Migraines commonly occur before and during menstruation and may last from several hours to three days. Migraines have been associated with irritation of the trigeminal nerve (in the face), a spreading depolarization in brain, low serotonin levels in the brain, and vasoconstriction in the brain.

Premenstrual Headaches:

Prior art attention to premenstrual headaches is minimal, and prior art treatment methods are minimal. The entire Medscape article on managing premenstrual syndrome (Moline and Zendell, "*Evaluating and Managing Premenstrual Syndrome*", 2000, *Medscape*) has only a single sentence relating to treatment of premenstrual headaches which reads: "Women with premenstrual headaches should try any of the common nonprescription analgesics (aspirin, acetaminophen, ibuprofen) at the onset of the headache."

Premenstrual Migraines:

Prior art has given considerably more attention to premenstrual migraine headaches and numerous observations and theories about both migraines and premenstrual migraines exist.

One of the first theories to explain migraines was the classic theory of vasoconstriction/vasodilation—more specifically that migraines were caused by constriction of blood vessels in the brain, followed by dilation. Brain studies during migraine have shown that blood flow to the brain is abnormal.

The theory of hyper excitability built on the idea of vasoconstriction/vasodilation by adding that migraine sufferers were extra susceptible to normal triggers, such as stress. During periods of excitability, more calcium flows from extracellular fluid to intracellular space, resulting in vasoconstriction. This theory was bolstered by studies that calcium channel blockers could prevent migraine.

Irritation of the trigeminal nerve has also been implicated in migraines. Activation of the trigeminal nerve by compounds such as nitroglycerine or capsaicin triggers migraines, lending credence to the involvement of the trigeminal nerve in migraine headaches.

A spreading area of depolarization in the cortex has also been associated with migraines, which may begin 24 hours before an attack, with the onset of the headache occurring around the time of the largest area of the brain is depolarized.

Serotonin has also been implicated in migraines, as serotonin levels in the brain are low during migraines. This theory is bolstered by the fact that serotonin agonists, such as triptans, can provide pain relief.

Although no single theory exists under prior art to explain migraines, numerous treatments exist, that provide varying degrees of relief. Migraine medications include serotonin agonists, nonsteroidal anti-inflammatory drugs, combinations of over the counter pain killers, ergot alkaloids, corticosteroids, botox injections, opiate analgesics, lidocaine applied in the nasal cavities, magnesium, butterbur root, feverfew, riboflavin (vitamin B 2), coenzyme Q10, and S-adenosyl-L-methionine.

Menstrual migraines are more specifically tied to the ovulation cycle, and are triggered during declining estrogen levels, although some women are thought to suffer migraine from the progesterone decline.

A comprehensive synopsis of prior art work related to ovarian hormones and the pathogenesis of menstrual migraine is contained in the Martin and Behbehani article enclosed under IDS (Martin V T MD and Michael Behbehani, PhD, "*Ovarian Hormones and Migraine Headache: Understanding Mechanisms and Pathogenesis—Part I*", © 2006 Blackwell Publishing, *Medscape* Jan. 26, 2006). Migraines are 3 times as common in women than in men and migraine attacks are commonly triggered by declines in serum estrogen levels. Accordingly, prior art menstrual migraine research is focused on ovarian hormone effects on A) serotonergic, B) noradrenergic, C) glutamatergic, D) GABAergic, and E) opiatergic systems, as disclosed in the article. The article then considers other possibilities, focusing on ovarian hormone effects on specific structures relevant to migraine headache such as meningeal arteries and the trigeminal nerve. A synopsis of the prior art synopsis is provided for reference:

A) Serotonergic. Serotonin 5-hydroxytryptamine; 5-HT) is a neurotransmitter that acts on seven distinct families of 5-HT receptors (5-HT1 to 5-HT7) and each receptor has multiple subtypes. Under prior art "Substantial evidence exists to suggest that the serotonergic system is important in the pathogenesis of migraine headache. A positron emission tomography (PET) study demonstrated increased serotonin synthesis capacity throughout all regions of the brain in migraine patients as compared to controls. Medications which are agonists of the 5HT1B, 5HT1D, and 5-HT1F receptors are efficacious abortive treatments for migraine headaches" (Martin and Behbehani).

Prior art has also demonstrated that estrogen effects serotonin by three pathways. First, estrogen treated monkey showed a nine-fold increase in tryptophan hydroxylase (TPH), the rate-limiting enzyme in synthesis of serotonin. Second, the serotonin reuptake transporter (SERT) removes serotonin from the synaptic cleft to terminate serotonergic transmission. Short term estrogen treatment of monkeys decreased amounts of SERT mRNA and longer treatments led to increased amounts of SERT mRNA. Third, monoamine oxidases, the primary enzymes that degrade serotonin, were reduced in monkeys receiving estrogen. Less compelling evidence suggests estrogen/progesterone combinations may modulate gene expression and binding potentials of serotonin receptors.

B) Noradrenergic System. The Martin and Behbehani article discloses that estrogen has been shown to up-regulate production of noradrenaline by up-regulating gene expression of tyrosine hydroxylase, a rate-limiting step in the production of noradrenaline. Studies also exist to show that estrogen may effect various subtypes of adrenoreceptors. The article also discloses that noradrenaline levels are decreased in migraineurs during headache free periods, suggestive of a state of chronic sympathetic hypofunction. Other studies imply that estrogen alone reduces central sympathetic activity, but the addition of progesterone may actually increase sympathetic tone.

C) Glutamatergic System. Glutamic acid is the major excitatory neurotransmitter in the central nervous system (CNS). The studies reviewed by Martin and Behbehani indicate that estrogen is a significant facilitator of the glutamatergic system and that certain effects can be attenuated by addition of progesterone.

D) GABAergic System: GABA is the major inhibitory neurotransmitter in the CNS. In vitro studies indicate that both estrogen and progesterone modulate GABAergic neurons. In vivo, women with premenstrual dysphoric disorder (PMDD) demonstrated increased cortical GABA during luteal phase (when both estrogen and progesterone levels are high) when compared to follicular phases (when estrogen is high but progesterone is low). The control group showed the opposite results with higher GABA levels in the follicular phases than the luteal phases.

E) Opiatergic System: The opiatergic system is important for pain control and regulation of reproductive behavior. Estrogen has been shown to increase levels of spinal cord enkephalin and enhance neuronal responsiveness of certain opioid receptors.

The article also covers other prior art theories by reviewing effects of ovarian hormones on specific structures relevant to migraine headaches.

Trigeminal Nerve: The trigeminal nerve is know to be involved in migraine headaches. The effects of ovarian hormones on the trigeminal nucleus caudalis (TNC) have been well studied. Animal model data show greater response magnitude and response duration of TNC neurons (i.e. enhanced sensitivity) is observed when estradiol and progesterone levels are high. It should be noted this is inconsistent with a premenstrual migraine, as falling levels of both hormones would predict reduced sensitivity of the TNC. However, TNC hypersensitization is consistent with falling estrogen levels under the novel etiology provided in present invention.

Brainstem Nuclei: The Martin and Behbehani article also postulate that ovarian steroids could potentially modulate neurotransmission within the brainstem nuclei to account for the increased blood flow to the dorsal pons observed on PET scans during spontaneous migraines.

Autonomic Nervous System: Estrogen alone reduces central sympathetic activity, reducing heart rate and sympathetic tone, while increasing parasympathetic tone. Addition of progesterone increases sympathetic tone. Chronic sympathetic hypofunction during headache-free period has been suggested in 10% to 15% of migraineurs.

Vascular Endothelium: Estrogen produces vasodilation through endothelium-dependent and non endothelial dependent mechanisms. The article suggests TNC sensitization by vasodilation of meningeal arteries.

Cortex: The anterior cingulate and insular cortices are activated on PET studies during a migraine attack. The article suggests ovarian steroids may modulate migraine on a cortical level.

Prostaglandin levels have also been associated with premenstrual/menstrual conditions, however, under prior art, the focus has been on the relation of prostaglandins and primary dysmenorrhea (menstrual cramping). Women with primary dysmenorrhea have increased activity of the uterine muscle with increased contractility and increased frequency of contractions. Cramping associated with dysmenorrhea usually begins a few hours before the start of bleeding and may continue for a few days. Prior art dysmenorrhea treatment methods center around prostaglandin inhibition. Prostaglandin levels have been found to be higher in women with severe menstrual pain than in women who experience mild or no menstrual pain. Non-steroidal anti-inflammatory drugs (NSAIDs) that inhibit prostaglandin synthesis can provide relief and include drugs such as Naproxen, Ibuprofen, and Mefenamic Acid. However, many NSAIDs can cause gastrointestinal upset as a side effect and COX2 inhibitors are sometimes prescribed instead. Oral contraceptives are effective in preventing dysmenorrhea as they suppress ovulation and menstruation.

Seizures:

According to the Epilepsy Foundation, recurring seizures are generally a symptom of epilepsy and in about 70% of people with epilepsy, no cause can be found. In the remainder, causes include head injuries, brain damage from hypoxia at birth, brain tumors, lead poisoning, genetic conditions such as tuberous sclerosis, and infections such as meningitis or encephalitis. The intermittent burst of electrical activity are much more intense than usual and may occur in just one area of the brain (partial seizures) or may affect nerve cells throughout the brain (generalized seizures). Seizures are often associated with sudden and involuntary contraction of a group of muscles.

The "Seizure Threshold" concept holds that "everyone has a certain balance (probably genetically determined) between excitatory and inhibitory forces in the brain. The relative proportions of each determine whether a person has a low threshold for seizures (because of the higher excitatory balance) or a high threshold (because of the greater inhibition). According to this view, a low seizure threshold makes it easier for epilepsy to develop, and easier for someone to experience a single seizure." (Epilepsy Foundation, http.//www.epilepsyfoundation.org/about/science/index.cfm, provided under IDS). Prior art anti-seizure medications work by modulating the balance between these excitatory and inhibitory forces in the brain.

Seizures, and the prior art drugs used to treat them, will be reviewed in light of the novel etiology/pathogenesis of present invention for consistency.

BRIEF SUMMARY OF THE INVENTION

The present invention discloses a novel underlying etiology/pathogenesis that results in headaches, migraines, and seizures. The present invention will explain the prior art observations in context of the new pathogenesis and will explain why prior art drugs used to treat migraines and seizures are consistent with the pathogenesis of present invention. Based on the novel disclosures, novel, more potent etiology based treatment methods are provided.

More specifically, present invention discloses that changes in certain endocrine levels result in alterations in the bone micro environment which in turn results in elevated extracellular calcium concentrations which in turn result in hypersensitization of nerves and hypercontractility of muscles that result in headaches, migraines, and increased seizure risk in people with low seizure thresholds. The present invention will cover several common endocrine oscillations (estrogen, testosterone, prostaglandins, 1,25 Vitamin D) and disclose the resulting pathogenesis that leads to alterations in the nerve and muscle micro environments that result in headaches, migraines, and seizures. Based on the disclosures provided, novel treatment methods that focus on modulating the bone microenvironment as a treatment for seizures and migraines will be provided.

DETAILED DESCRIPTION OF THE INVENTION

Overview

Figure 1:
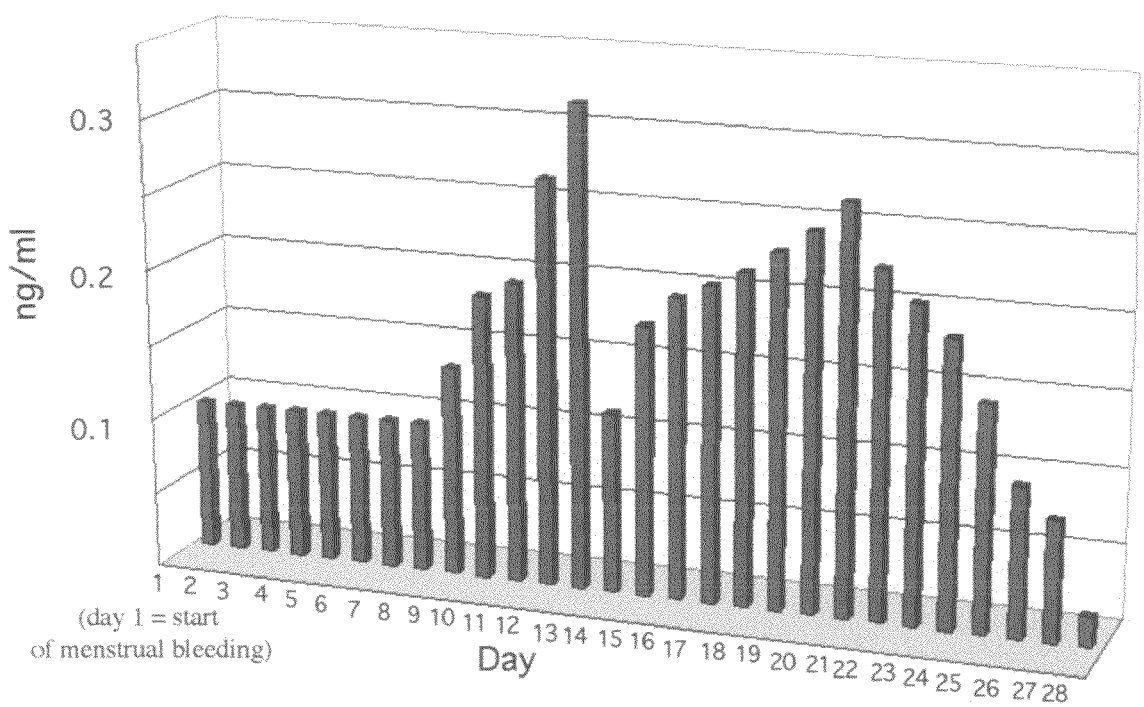
FIG. 1 shows estrogen levels during the ovulation cycle.

Prior art has focused on numerous possible pathophysiologies for migraines, yet no single prior art theory can explain all of the symptoms and observations. Prior art does not know what causes 70% of seizures.

In contrast, present application presents a single underlying event that occurs, which in turn effects several physiological systems, which in turn accounts for all of the symptoms and observations.

The present invention discloses how common endocrine oscillations (e.g. estrogen, testosterone, prostaglandins, 1,25 vitamin D) can alter the bone microenvironment, which in turn results in a transient elevation in Ca2+ levels, which in turn results in hypersensitization of nerves and muscles that result in headaches, migraines, and seizures.

Novel treatment methods are then provided that target the underlying etiology/pathogenesis.

The Bone Micro Environment

Because the underlying pathogenesis of present invention starts with the oscillation in the endocrine levels affecting the bone micro environment, a brief background of the bone micro environment is provided for reference.

Normal bone undergoes a continual remodeling process that essentially replaces the entire skeleton every 10 years. Remodeling is mediated by two cell types, osteoclasts which dissolve bone (resorption), and osteoblasts which are the bone builders. Both cell types come together in three to four million remodeling sites scattered throughout the skeleton. During childhood and adolescence, bone formation proceeds at a faster rate than resorption. By around age 40 bone resorption begins to outpace bone formation and bone thinning begins to manifest. On average, women attain a peak bone mass that is about 5% below that of a man, so they have less "in the bank" to start with at the onset of age related bone loss. For this and other reasons, risk of osteoporosis (literally "porous bone") is greater in women, who account for 80% of cases.

Osteoblasts (the bone building cells) secrete collagen and other bone proteins creating a matrix onto which calcium, phosphorous, and other minerals crystallize (~90% of bone mass), which removes calcium from extracellular fluid and blood circulation. Osteoclasts (the bone dissolving cells) secrete both proteolytic and hydrolytic enzymes and hydrochloric acid that result in destruction of the bone's protein matrix, which results in mobilization of calcium, phosphorous, and bone resident growth factors, into the extracellular fluid. The cyclicality of bone destruction followed by bone building appears to be an important aspect required for maintenance of bone density. Intermittent administration of parathyroid hormone (PTH), which increase osteoclast activity, results in an eventual increase in bone mass (whereas continued administration results in bone loss).

In addition to providing structural support and organ protection, bone serves as a repository of calcium and is used to maintain serum calcium concentrations. The average adult human body contains 1.3 kg of calcium of which 99% is contained in bones and teeth, 1% in cells of soft tissue, and 0.15% in the extracellular fluid. Normal serum plasma levels of calcium range from 8.0 to 10.8 mg/dl (2.2 to 2.7 mmol/L) with 40%-43% bound to plasma proteins, 5%-10% combined with anions such as phosphate and citrate to form non ionized complexes, and the remaining 40%-50% being free ionized calcium. Because of the large reservoir of bone calcium (i.e. 99%), versus the extremely small extracellular amount (i.e. 0.15%), perturbations resulting in the release of reservoired bone calcium have the potential for profound transient effects on extracellular calcium concentrations.

The primary hormone responsible for increasing serum concentrations of calcium is parathyroid hormone (PTH) and the primary hormone responsible for reducing serum concentrations of calcium is calcitonin, which is produced by the parafollicular cells of the thyroid. When calcium sensors in the parathyroid gland detect low serum calcium concentrations, production of PTH is upregulated, resulting in upregulated osteoclastic activity and increased renal reabsorption of calcium. High serum calcium concentrations result in upregulated production of calcitonin, resulting in decreased osteoclastic activity and up to a 5 fold increase in renal excretion of calcium.

In addition to calcium, phosphorus and various growth factors are also stored in the bone, and are mobilized into the extracellular fluid by osteoclast activity. The calcium to phosphorous ratio in bone is 2.5 to 1 and phosphorus is involved in numerous physiological processes including transport of cellular energy via adenosine trisphosphate (ATP), phosphorous is important for key regulatory events such as phosphorylation, and phospholipids are the main structural components of cellular membranes. Phosphorous is also used in maintenance of extracellular/intracellular ion concentration gradients via transmembrane ATPase pumps. Growth factors that are stored in bone and liberated by osteoclast activity include platelet-derived growth factors (PDGF), fibroblast growth factors (FGF), insulin like growth factors (IGFs) I and II, transforming growth factor-beta (TGF-beta), endothelin 1 (ET-1), urokinase type plasminogen activators, and others. The growth factors released from bone are potent mitogens. PDGF and FGF are mitogens that stimulate progression of many cell types through the early part of the G-1 Phase and IGF-1 and IGF-2 are potent mitogens that promote cell progression through the later part of the G-1 Phase. It is believed the release of these growth factors plays a crucial role in stimulating osteoblast development, required for bone rebuilding.

Osteoblasts arise from osteoprogenitor cells located in the bone marrow and periosteum. Osteoprogenitors are induced to differentiate under the influence of growth factors, including the bone morphogenic proteins (BMPs), fibroblast growth factor (FGF), platelet-derived growth factor (PDGF), transforming growth factor beta (TGF-β).

Osteoclasts arise through the differentiation of macrophages. Osteoclasts are regulated by several hormones including PTH from the parathyroid gland, calcitonin from the thyroid gland, estrogen, vitamin D, and growth factor interleukin 6 (IL-6). Osteoclast population density is modulated by three molecules produced by osteoblasts—two that promote osteoclast development and one that suppresses osteoclast development. The two osteoclast promoter molecules are 1) macrophage colony-stimulating factor that binds to a receptor on macrophages inducing them to multiply and RANKL (receptor activator of NF-kB ligand) that binds to a different receptor (RANK receptor) inducing the macrophage to differentiate into an osteoclast. The molecule that inhibits osteoclast formation is osteoprotegerin (OPG), which blocks osteoclast formation by latching on to RANKL and blocking its function.

Osteoclast activity is modulated by various compounds through the following pathways.

PTH interacts with its receptor on osteoblasts to upregulate production of RANKL, which upregulates macrophage differentiation into osteoclasts. Additionally, PTH increases calcium reabsorption by the renal tubules and stimulates conversion of vitamin D to its active form (calcitriol).

Calcitonin receptors have been found in osteoclasts and osteoblasts and single injections of calcitonin result in the loss of the ruffled osteoclast border responsible for resorption of bone and a marked transient inhibition of the ongoing bone resorptive process. Calcitonin also increases renal excretion of calcium by decreasing reabsorption by the kidneys and evidence exists that it reduces absorption of calcium in the gastrointestinal tract.

Estrogen has a "triple whammy" (Rosen C J, "*Restoring Aging Bones*", *Scientific American*, March 2003) effect in inhibiting osteoclast activity by binding to osteoblasts and 1) increasing their output of OPG and 2) suppressing their RANKL production. In addition, estrogen appears to prolong lives of osteoblasts while simultaneously 3) promoting osteoclast apoptosis. As estrogen levels drop after menopause, these "brakes" on osteoclast inhibition are removed, tipping the balance in favor of osteoclast dominated bone destruction which results in osteoporosis.

Androgens also have an inhibitory effect on bone resorption, and studies suggest that this occurs through local aromatization of androgens into estrogen, however direct androgen interactions with androgen receptors (AR) related to bone remodeling have been observed in animal models.

Vitamin D is a steroid-like chemical that promotes osteoclast activity by binding to vitamin D receptors (VDR) in osteoblasts and upregulating expression of RANKL. Vitamin D also enhances intestinal absorption of calcium and enhances renal retention of calcium.

Estrogen, Bone, and Extracellular Calcium Levels

Serum estrogen levels vary throughout the ovulation cycle as shown in FIG. 1, which is excerpted from a reference text graph of ovulation hormone levels (*Biochemical Pathways*, edited by Gerhard Michal, Wiley & Sons, 1999, page 205, FIG. 17.1-6). Beginning about 20 days prior to the start of menstrual bleeding, estrogen levels rise to double to triple the levels observed during menstruation. A few days prior to start of menstrual bleeding, estrogen levels begin to decline, with the most precipitous decline occurring the day before the start of menstrual bleeding.

Figure 2:
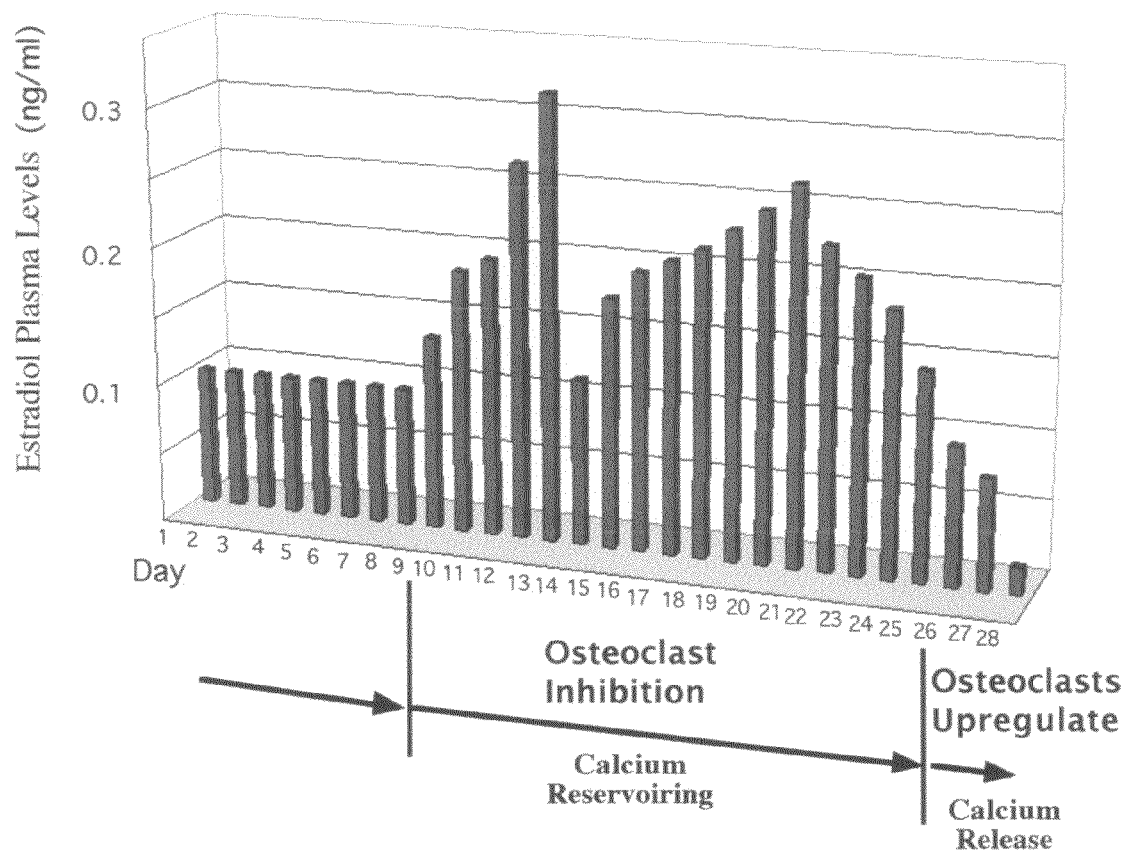
FIG. 2 shows estrogen's effect of "reservoiring" and "release" of calcium and growth factors (via osteoclast population density modulation) during the ovulation cycle

From osteoporosis research, it is known that estrogen inhibits osteoclast activity by at least 3 pathways (i.e. the "triple whammy" previously disclosed). Accordingly, elevated estrogen levels tip the balance in favor of osteoblast activity, which result in net bone building activity, which in turn includes storage of calcium and growth factors in bone. This is referred to as "reservoiring" in this application and occurs during the time estrogen levels are elevated as shown in FIG. 2. The subsequent drop in estrogen levels removes the inhibitory effects on osteoclasts, which tips the balance in favor of bone resorption activity, which in turn includes release of calcium and growth factors along the approximate timeline shown in FIG. 2.

The most precipitous decline in estrogen levels occurs a day or so prior to the start of menstrual bleeding, and accordingly the highest release of bone resident calcium would also occur around this time, hereinafter referred to as the "calcium spike". As extracellular concentrations of calcium begin to rise, the concentrations work their way through into blood circulation, where the escalating serum concentrations activate the body's serum calcium control mechanisms (via calcitonin). Blood calcium concentrations are tightly controlled (unlike extracellular concentrations the have a greater range of variability) and renal excretion of serum calcium can increase 5 fold (provided it does not get overwhelmed ) to maintain serum calcium homeostasis and osteoclasts activity is inhibited (osteoclasts lose their ruffled border that dissolves bone) to reduce the amount of calcium being mobilized from the bone into the extracellular fluid.

Although calcitonin has significant calcium lowering effects in some species, in humans, calcitonin's influence on blood calcium levels is much smaller. Human calcitonin is not used for management of hypercalcemia, instead salmon calcitonin is used, as it is around 40-50 times more potent than human calcitonin and has a longer duration of action. Despite the higher potency of salmon calcitonin, its effects on reducing serum calcium levels are often inadequate to manage conditions such as hypercalcemia of malignancy, requiring the use of even more potent drugs such as bisphosphonates that induce osteoclast apoptosis.

Accordingly, the naturally weak human calcitonin based serum $Ca^{2+}$ downregulation system would likely be playing catch-up with the progressively elevating $Ca^{2+}$ release caused by the premenstrual estrogen decline. Furthermore, the rising extracellular calcium concentrations would not have the direct benefit of renal clearance that blood circulation does, and there would be much sharper escalations in extracellular calcium concentrations than in blood. This is important to note, as extracellular calcium concentrations (and more specifically concentrations surrounding nerve and muscle membranes) are of primary importance to present invention, and not blood concentrations.

The worst peak in calcium concentrations would occur the day prior to start of menses (i.e. as a result of the sharp premenstrual estrogen drop), after which point calcium levels would start normalizing as estrogen levels normalized and calcitonin would have finally caught up and eventually managed to work its way back to reducing extracellular calcium concentrations.

Extracellular Calcium and the Nervous System

Transiently increased extracellular $Ca^{2+}$ levels effectively "hypersensitize" nerves by three pathways described below.

The fundamental task of a neuron is to receive, conduct, and transmit signals. Neurons can be classified by function into sensory neurons, motor neurons, or interneurons, however they all have the same overall structure. Neurons have a spherical central cell body (soma) that contains the typical organelles found in all cells, branching dendrites on one side to receive signals, and a long axon on the other side for transmitting information. The axon commonly divides into many branches at its far end so it may pass the message to many target cells simultaneously. A signal travels along the neuronal membrane as an electrical pulse until it reaches the end of the axon, where typically the electrical pulse results in neurotransmitter release across the synapse, which in turn results in an electrical pulse being induced in the next neuron.

Neurons contain ion channels that maintain a balance between potassium, sodium, and chloride so that the resting membrane potential inside of the neuron is around −85 mV relative the outside of the cell (ranges from −30 mV to −100 mV depending on cell type). The cell membrane acts as a capacitor, storing charge separated by the thickness of the membrane, and has a typical capacitance of about 1µ Farad per square centimeter. Changes to the membrane potential are called "depolarizing" if they make the inside of the cell less negative or "hyperpolarizing" if they make the inside of the cell more negative. Electrical impulses that travel along the neuron are called action potentials and are transient perturbations in the membrane potential. Action potentials are conducted in a all-or-none manner and for an action potential to be generated the input signal must depolarize the neuron by more than its "threshold" membrane potential. As an example, for the −85 mV resting membrane potential neuron above, the threshold voltage is around −70 mV, meaning that the input signal must depolarize the membrane by at least 15 mV to generate a nerve impulse (i.e. action potential).

Changing the extracellular or intracellular concentrations of ions changes the resting membrane potential. Depolarizing concentrations (i.e. that make the inside of the cell less negative) bring the resting membrane potential closer to the threshold potential, and consequently the neuron requires a smaller input voltage to trigger an action potential. Polarizing concentrations (those that make the inside more negative) move the resting membrane potential farther away from the threshold potential and result in a larger input signal being required to trigger an action potential.

A traveling nerve impulse opens voltage gated Na+ channels and K+ channels, which allow Na+ to flow into the cell and K+ to flow out of the cell, passively along their respective electrochemical gradients. Both the Na+ channels and K+ channels are rapidly inactivated by a "ball and chain" amino acid complex that rapidly plugs the respective channels. Potassium (K) is the most significant ion in impulse transmission because of the large disparity between the extracellular and intracellular concentrations. Typical extracellular concentrations potassium and sodium are about 3 mM of K+ and 117 mM of Na+ and the typical intracellular concentrations are about 90 mM of K+ and 30 mM of Na+. The 30 fold concentration gradient disparity of K+ (i.e. 90/3) overwhelms the 4 fold gradient disparity of Na+ (i.e. 117/30).

The resting (equilibrium or E) membrane potential for a given ion (e.g. potassium) can calculated using the Nernst equation:

$$E_k = RT/zF(\ln([K]_o/[K]_i))$$

where:
Ek is the equilibrium (or resting) membrane potential for potassium
R is the gas constant (8.31 joules/mole/° K)
T is the absolute temperature (Kelvin=273+° C.)
z is the valence of the ion (+1 for potassium)
F is the Faraday constant (amount of charge on a mole of ions, 96,500 coulombs/mole)
Ko is the outside (extracellular) concentration of potassium (in mM) and
Ki is the inside (intracellular) concentration of potassium At room temperature (20° C.=293° K) and for potassium:

$$RT/zF=(8.31)(293)/(+1)(96,500)=0.02523\ V=25\ mV$$

and for concentrations of 3 mM outside the cell and 90 mM inside the cell:

$$E_k=(25\text{ mV})(\ln([K]_o/[K]_i))=(25\text{ mV})(\ln 3/90)=(25\text{ mV})(-3.4)=-85\text{ mV}$$

The effect of elevating extracellular concentrations of positive ions can be seen from the Nernst equation. Increasing extracellular concentration of the positive ion K+ results in a more positive resting membrane potential, which is by definition depolarizing, and brings the resting membrane potential closer to the threshold potential. This means a smaller input signal voltage is required to trigger the "all-or-none" action potential.

As an example, as extracellular concentrations of K+ are raised to 4 mM, the resting membrane potential becomes more positive:

$$E_k=(25\text{ mV})(\ln(4/90))=(25\text{ mV})(-3.11)=-78\text{ mV}$$

Using the −70 mV threshold voltage, the input voltage required to initiate an action potential is now only 8 mV versus 15 mV. Applicant refers to this as "neuronal membrane hypersensitization" in present application.

The actual resting membrane potential is a summation of all ions that are permeable and can be more precisely calculated using the Goldman Hodgkin Katz equation (GHK) for computing the resting membrane potential:

$$V_m = 58\log\frac{(pk[K]o + pNa[Na]o + pCl[Cl]i)}{(pk[K]i + pNa[Na]i + pCl[Cl]o)}$$

Where:
$V_m$ is the resting membrane potential.
pI is the permeability of an ion.
[I]o is the extracellular concentration of an ion.
[I]i is the intracellular concentration of an ion.

The GHK equation above does not include $Ca^{2+}$, however, since calcium ions are permeable through the sodium-calcium exchanger, for precise calculations, $Ca^{2+}$ would need to be included in the above GHK equation.

Alternatively, the Nernst equation provides a good way of estimating an individual ion's contribution to the overall resting membrane potential.

From the Nernst equation, we can see that increasing extracellular concentrations of positive ions, relative to intracellular concentrations of positive ions, is a depolarizing change. Accordingly, elevating extracellular $Ca^{2+}$ levels relative to intracellular $Ca^{2+}$ levels is a depolarizing event that would lead to neuronal membrane hypersensitization (i.e. reducing the magnitude of the input signal required to initiate an action potential).

Neuronal intracellular calcium ($Ca^{2+}$) levels are kept low as calcium is a signaling molecule within a neuron (used for neurotransmitter release at the synapse). Calcium ATPase pumps in the cell membrane and in the membranes of intracellular organelles pump calcium out of the cytoplasm. Extracellular concentrations of $Ca^{2+}$ can range from 1 to 2 mM (*Molecular Biology of the Cell*, Garland Publishing, third edition, p. 508). However, intracellular concentrations are kept very low and do not increase proportionately relative to extracellular increases. Studies of mammalian brain nerve cells showed that as extracellular concentration of $Ca^{2+}$ were raised from 1 mM to 2mM, the intracellular concentrations only rose from 130 nM to 160 nM, respectively (Nachshen D A, "*Regulation of cytosolic calcium concentration in presynaptic nerve endings . . .*" *J. Physiol*. June 1985; 363: 87-101, FIG. 1B on page 90). Accordingly, for a 100% increase in extracellular concentrations of $Ca^{2+}$, the intracellular concentrations only rise 25%.

From the above information we can approximate the amount of depolarization that would occur across the range of 1 mM to 2 mM of extracellular $Ca^{2+}$. Using the Nernst equation and the change in the $E_{Ca}$ between the 2 nM and 1 nM levels would provide the amount of depolarization in mV that could be expected (per 1 mM) over this range (i.e. $E_{Ca}$ @2 mM -$E_{Ca}$ @1 mM=net change in resting membrane potential from a 1 mM change in extracellular $Ca^{2+}$ concentrations), or:

$$\Delta E_{Ca} \text{ per 1 mM increase in } [Ca]_o = E_{Ca}\text{ @2 mM}-E_{Ca}\text{ @1 mM}$$

For calcium, RT/zF=(8.31)(293)/(+2)(96,500)=12.6 mV and the $$\Delta E_{Ca} = (12.6\text{ mV})(\ln(2/.000160)) - (12\text{ mV})(\ln(1/.000130))$$
$$= (12.6\text{ mV})(9.43) - (12.6\text{ mV})(8.948)$$
$$= +6.12\text{ mV}$$

Accordingly, the increase in extracellular $Ca^{2+}$ concentrations from 1 mM to 2 mM would make the resting membrane potential more positive by around 6 mV. In our previous example, this would reduce the resting membrane potential from −85 mV to −79 mV, which in turn would reduce the amount of input stimulus required to trigger a nerve impulse from 15 mV to 9 mV.

This neuronal membrane hypersensitization disclosed above is the first mechanism by which rising calcium ion concentrations would affect the nervous system.

The second mechanism is calcium related neurotransmitter release, as it relates to both sensory receptor transduction signaling and synaptic gap signal transmission.

As a nerve impulse reaches the synapse, voltage gated $Ca^{2+}$ channels open which allow an inrush of $Ca^{2+}$ to enter the pre synaptic cell, along its electrochemical concentration gradient.

Neurotransmitter is stored in vesicles and $Ca^{2+}$ causes the vesicles to fuse with the cell membrane, releasing the neurotransmitter by exocytosis into the synaptic cleft. The neurotransmitter binds to and opens transmitter-gated ion channels on the post synaptic cell, which triggers a depolarization in the post synaptic cell, triggering an action potential if sufficient depolarization occurs. The extent of the depolarization of the post synaptic cell is graded according to how much neurotransmitter is released at the synapse and how long it persists there (*Molecular Biology of the Cell*, Garland Publishing, third edition, p. 536).

As extracellular $Ca^{2+}$ levels increase from 1 mM to 2 mM, not only does the absolute amount of molecules available to rush in through the voltage gated channels double, but the concentration gradient (i.e. the driving force for the inrush) increases 63% from being 7,672 times greater on the outside at 1 mM (i.e. 1 mM/130 nM) to being 12,500 times greater on the outside at 2 mM (i.e. 2 mM/160 nM). Accordingly, the much larger amount of $Ca^{2+}$ entering the pre synaptic cell during the transient period when the voltage gated channels are open would result in much greater release of neurotransmitter. Since depolarization of the post synaptic cell is graded and related to the amount of neurotransmitter released, as previously disclosed, the effect of rising extracellular $Ca^{2+}$ levels would also be "hypersensitization of synaptic gap transmission" via greatly "upregulated neurotransmitter release" from the pre synaptic cell combined with the "neuronal membrane hypersensitization" in the post synaptic cell (i.e. the depolarization per the Nernst equation). Accordingly, rising extracellular calcium concentrations would have a direct "double whammy" effect on nerves.

A third mechanism, known as posttetanic potentiation (PTP), can also cause over-excitation in brain neurons form increased transmitter release related to the inability of the neurons to clear the $Ca^{2+}$ inrush in a timely manner. PTP occurs normally in response to a long high frequency train of action potentials (e. g. 100 action potentials per second for 15 seconds). A tetanic train of potentials will cause a large increase in the concentration of cytoplasmic calcium that cannot be readily cleared. This calcium will then travel down the mitochondrial calcium uniporter to increase the mitochondrial calcium levels. After the tetanic train, cytoplasmic calcium will be pumped out of the cell and when the cytoplasmic level is low enough, calcium from the mitochondria enters the cytoplasm. While this happens, any action potential that occurs in this time frame, will cause more transmitter release, because of the elevated intracellular calcium levels (i.e. PFP). In other word, the higher levels of intracellular calcium result in larger amounts of neurotransmitter being released in response to neuronal depolarization. This increases the strength and duration of the signal in the brain for a given level of stimulus. Elevated levels of extracellular calcium could be expected to exacerbate PTP type un-cleared intracellular calcium levels, as well as reduce the frequency and duration of the input train of action potentials required to trigger this condition.

The term neuronal "hypersensitization" is hereinafter used to describe the effect of elevated extracellular calcium levels on nerves via 1) neuronal membrane depolarization, 2) upregulated neurotransmitter release at synapses, and 3) PTP mechanisms.

Extracellular $Ca^{2+}$ levels also have a direct effect on muscle tissue, discussed below.

Extracellular Calcium and Muscles

Transiently elevated extracellular calcium levels would increase muscle contraction by two pathways.

The first relates to nerves and the neuromuscular junction. Muscle contraction is triggered by a nerve impulse traveling down a neuron which is then converted to a release of the neurotransmitter acetylcholine at the synapses where the neuron meets the muscle. Enhanced neurotransmitter release results when extracellular $Ca^{2+}$ levels are high, by the voltage gated $Ca^{2+}$ channel pathways previously disclosed above. Accordingly, more acetylcholine is released at the neuromuscular junction, causing a greater post synaptic depolarization.

The second pathway relates to extracellular $Ca^{2+}$ concentration's direct effect on muscle contraction. The release of the neurotransmitter acetylcholine described above causes the muscle to depolarize via neurotransmitter gated channels. The depolarization spreads along the muscle surface and the T-tubules that run along the surface of the muscle fibers. The depolarization opens voltage gated $Ca^{2+}$ channels in the T-tubule surface that allows $Ca^{2+}$ from the extracellular fluid in the T-tubule to enter the the sarcoplasmic reticulum. The inrush of $Ca^{2+}$ into the sarcoplasmic reticulum activates the "sarcoplasmic reticulum calcium release channels" (SR-CaRCs), which in turn release $Ca^{2+}$ into the fluid around the myofibrils. The released $Ca^{2+}$ allows the muscle to contract by removing the tropomyosin block between actin and myosin, triggering cross-bridge formation by enabling myosin to bind to actin.

With an increase in the extracellular calcium concentration, there will be a larger release of $Ca^{2+}$ from the T-tubules, which in turn will activate more SRCaRCs and the release of more $Ca^{2+}$ onto the myofibrils, which in turn will cause greater cross-bridge formation and muscle contraction.

Short Term Versus Long Term Effects

It should be noted that the above analysis is related to acute (i.e. transient or short term) rising calcium concentrations and nerve firing. Chronic (i.e. persistent or long term) elevated calcium and nerve firing would eventually deplete neurotransmitter availability. Neurotransmitter is degraded after release into the synapse and new neurotransmitter must be continually synthesized in the cytosol of the neuron. Chronic, excessive neurotransmitter release, and hence excessive neurotransmitter degradation, could result in depletion of neurotransmitter availability.

In muscles, the initial hypercontractility would be followed by eventual hypocontractility (i.e. relaxation, inability to contract in response to stimulus) upon neurotransmitter depletion. In nerves, the initial hypersensitization and enhanced nerve cell firing would eventually result in inhibition of nerve firing, both from neurotransmitter depletion and from membrane hyperpolarization from intense firing. During nerve firing, sodium and calcium flow into the nerve depolarizing the membrane, after which nerves briefly hyperpolarize, closing sodium and calcium channels and allowing potassium to rush out, "But neurons can remain excessively hyperpolarized, or inhibited, for a long time following intense stimulation." (Dodick and Gargus, "*Why Migraines Strike*", *Scientific American*, August 2008, p. 58).

Relevance to Migraines

Migraines are typically broken up into 4 phases (Dodick and Gargus). The first phase, called prodrome, is experienced by 60% of patients, and its symptoms include sensitivity to noise and light, difficulty concentrating, yawning, and fatigue and can last from several hours to a few days. The second phase, called aura, is experienced by only 30% of patients and includes visual illusions of sparks and lights, often followed by dark spots in the same configuration and can last from 20 to 60 minutes. The third phase is the headache, characterized by excruciating pain accompanied by sensitivity to light and sound, nausea and vomiting and can last from 4 to 72 hours. The fourth phase, called prodrome, is experienced by 70% of patients, includes persistence of sensitivity to light and movement, lethargy, fatigue and difficulty focusing, and can last a few hours to a few days.

Aura is associated with a wave of intense nerve cell activity that spreads through the cortex, especially the areas that control vision. This hyperexcitable phase is followed by a wave of widespread and relatively prolonged neuronal inhibition. (Dodick and Gargus).

In general, in context of pathogenesis of present invention, the prodrome is consistent with the initial elevation in extracellular calcium and nerve hypersensitization (e.g. the observed sensory hypersensitivity in prodrome). The aura, or hyperexcitable phase, is consistent with peak of the neuronal firing during the hypersensitization. The following cortical neuronal inhibition is consistent with the expected neurotransmitter depletion and membrane hyperpolarization following intense firing. The persistence of sensory hypersensitivity in the postdrome is consistent with the elevated, but now declining, calcium levels under pathogenesis of present invention.

More specifically, all of the detailed observations of most migraines can be explained in context of pathogenesis of present invention. "Two thirds of the world's 300 million migraine sufferers are women aged 15 to 55—suggesting estrogen plays a role" (Dodick and Gargus). Accordingly, a detailed review of menstrual cycle related migraines is presented below.

Clinical Corroboration—Headaches and Migraines and $Ca^{2+}$

In estrogen modulated nerve and muscle hypersensitization, via osteoclast modulated $Ca^{2+}$ release, we can view the symptoms and observations to see if they corroborate or contradict the underlying pathogenesis presented.

Clinical Corroboration—Premenstrual Headaches:

Hypersensitivity to Sound: The hypersensitivity to sound is consistent with the neuronal hypersensitization pathways disclosed above. Auditory stimulus would be abnormally amplified in the presence of elevated extracellular $Ca^{2+}$ levels. Accordingly, this symptom is consistent the presented pathogenesis.

Figure 3A:
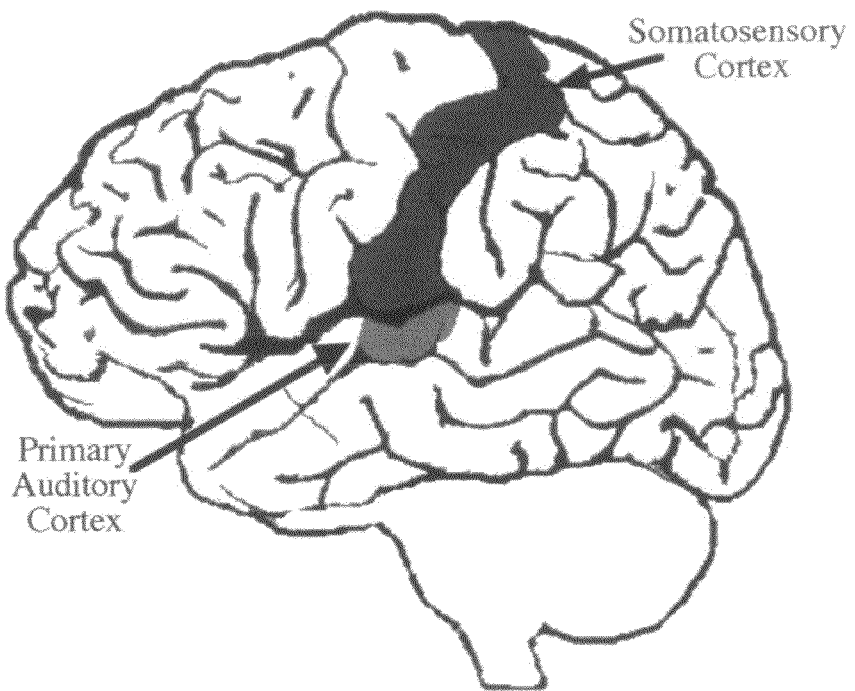
FIG. 3a shows the region of the brain where the somatosensory and auditory cortex are located and
FIG. 3b shows the mapping of peripheral sensory nerves to the somatosensory cortex.

Location of Headache: The location of the headache in the center of the head, and not pronounced at the front or back, is consistent with the location of the somatosensory cortex in the brain as shown in FIG. 3a (darker shaded area). The auditory cortex is just below the somatosensory cortex as shown in FIG. 3a (lighter shaded area). The continual signals from hyper sensitized sensory neurons would effectively result in a sensory "overload" in this region of the brain. Accordingly, the location of the headache is also consistent with the pathogenesis presented.

Desire for quiet, dark room and sleep to ameliorate the symptoms: This is consistent with the pathogenesis presented from two standpoints. First, the "sensory deprivation" provided by this environment would function to counteract the neuronal hypersensitization by depriving nerves of any stimulus at the very front end of the process. Second, the absence of light results in the downregulation of vitamin D synthesis (i.e. the sunshine vitamin) which in turn results in downregulation of serum $Ca^{2+}$ levels as previously disclosed (i.e. preventing vitamin D interaction with vitamin D receptors in osteoblasts prevents RANKL production via this pathway, which in turn downregulates osteoclast population density and the related release of $Ca^{2+}$ from bone).

Figure 3B:
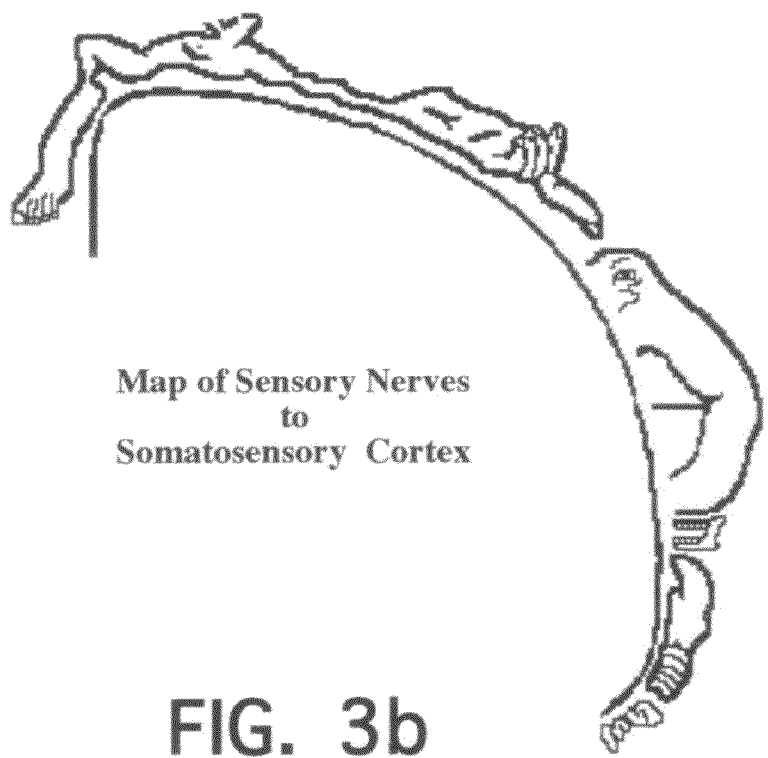

Clinical Corroboration—Premenstrual Migraines:

Trigeminal Nerve: Migraines have been associated with irritation of the trigeminal nerve. Migraines are triggered experimentally by compounds such as nitroglycerine which activates trigeminal nociceptors. The trigeminal nerve conveys sensory information for the face and much of the head. FIG. 3b shows the disproportionately large area of somatosensory cortex that maps to the face and head. The "irritation" of the trigeminal nerve is consistent with the hypersensitization of the trigeminal nerve system predicted by the elevated $Ca^{2+}$ levels as previously presented (i.e. $Ca^{2+}$ mediated membrane depolarization and $Ca^{2+}$ voltage gated channel mediated amplified neurotransmitter release).

Spreading Depolarization: A spreading area of depolarization in the cortex has been associated with migraines, which may begin 24 hours before an attack, with the onset of the headache at the time of the largest area of the brain is depolarized. This is consistent with the pathways presented under present invention, as the cortical depolarization would be predicted by the three pathways disclosed related to neuronal depolarization/hypersensitization from elevated $Ca^{2+}$ levels.

Vasoconstriction/Vasodilation: The hypersensitization of nerves and enhanced muscle contractions related to elevated $Ca^{2+}$ levels could also be expected to result in hyper vasoconstriction. Nerve signals to vascular smooth muscle cell would be amplified by 1) $Ca^{2+}$ motoneuron membrane depolarization, 2) motoneuron neurotransmitter release would be amplified via the voltage gated $Ca^{2+}$ channels at the synapse, and 3) the force of vascular smooth muscle contraction would be amplified in the muscle tissue itself via the amplified $Ca^{2+}$ release into the muscle fibers and the resulting amplified actin/myosin interactions. Vasodilation is consistent with eventual neurotransmitter depletion, as discussed above.

Low Cerebral Serotonin: As previously disclosed, low serotonin levels are observed during migraines and PET scans showed increased serotonin synthesis capacity in migraine patients. Serotonin is synthesized from the essential amino acid tryptophan via tryptophan hydroxylase and is degraded into 5-hydroxytryptophol or 5-hydroxyindoleacetic acid via the enzyme MAO. Pathogenesis of present invention is consistent with low serotonin levels during migraine as excessive firing from hypersensitized nerves throughout the body and in the brain would result in excessive release of serotonin at the synaptic clefts, which in turn would result in excessive degradation of serotonin. The serotonergic response is terminated by reuptake into the pre synaptic axon terminal and "The major pathways for the degradation of serotonin are reuptake into the nerve and degradation by MAO" (*Neuroscience In Medicine, Second Edition*, Humana Press, p. 472). Accordingly, the excessive serotonin release would be expected to result in excessive serotonin degradation and hence depletion (i.e. low levels) of serotonin over time. The observed increased serotonin synthesis capacity in migraineurs would also be consistent with the body's attempt to replenish the depleted serotonin levels.

Other Corroboration—Susceptibility to Underlying Etiology

Magnesium:

Magnesium deficiency is observed in 45% of women with menstrual migraine (Clayton A H MD, "*Menstrual Migraine*", Primary Psychiatry, 2006). This is consistent with the pathogenesis of present invention, as magnesium ($Mg^{2+}$) is a physiological calcium ($Ca^{2+}$) channel blocker (R. Loch Macdonald, "*Cerebral Vasospasm*" Thieme, 2005, p. 43). As a calcium channel blocker, magnesium would function antagonistically to $Ca^{2+}$ channel mediated effects such as enhanced neurotransmitter release and enhanced muscle contraction activity, previously disclosed. In relation to cerebral vasoconstriction, "hypo-magnesemia increases both calcium uptake and calcium release from the sarcoplasmic reticulum, causing vascular smooth muscle contraction" (Macdonald R L, *Cerebral Vasospasm*, Thieme, 2005, p. 44). In context of present invention, patients with low magnesium levels would be at a disadvantage in offsetting the "calcium spike" and hence more susceptible to the physiological effects that are mediated by $Ca^{2+}$ channels.

Low Calcium Levels During Luteal Phase:

U.S. Pat. No. 6,228,849 ('849) for PMS treatment methods discloses that "women with PMS had significantly lower calcium levels during the luteal phase of the menstrual cycle" (Col. 1, lines 47-49) and '849 claims administration of calcium and vitamin D as a treatment method for PMS. The observation of lower calcium levels during the luteal phase is consistent with pathogenesis of present invention as the luteal phase is when the estrogen levels are highest and calcium "reservoiring" occurs as shown in FIG. 2. It is the period when calcium would be removed from circulation and stored in bone, and lower calcium levels could be indicative of more aggressive reservoiring in some women, which could then be expected to result in more aggressive calcium release when the estrogen levels drop. The observations are consistent with the pathogenesis of present invention, and potentially point to yet another factor that may account for an exacerbated underlying etiology in certain patients (i.e. aggressive calcium reservoiring during the luteal phase eventually leads to higher calcium release prior to menstruation).

Hypothyroid:

In the 1980's, a research group found that 90% of their patients with PMS had 1 or more symptoms of hypothyroidism (Moline and Zendell, "*Evaluating and Managing Premenstrual Syndrome*", 2000, *Medscape*). However, a double blind study that administered levothyroxine (thyroxine), the major hormone secreted by the thyroid that controls the rate of metabolic processes, did not show any benefit over the placebo. The disappointing results apparently killed further research in this area. The present invention does not focus on thyroxine, but instead focuses on another thyroid hormone, calcitonin. Hypo production of calcitonin, the major hormone used for calcium level downregulation, would impair the body's ability to manage the elevating systemic calcium levels and "calcium spikes" in a timely manner. Hypo production of calcitonin would be expected to result in elevated $Ca^{2+}$ levels during the "calcium spike" and is consistent with the underlying pathogenesis presented.

In the same manner that changes in estrogen levels modulate the bone microenvironment and $Ca^{2+}$ levels, several other normal endocrine oscillations would also be expected to result in or contribute to migraines.

Testosterone, Bone, and Extracellular Calcium Levels

Drops in testosterone levels would follow the same pathogenesis as presented above for drops in estrogen levels.

Testosterone is aromatized into estrogen to achieve osteoclast inhibition, and some studies have also shown a direct effect of testosterone on osteoclast inhibition. A drop in testosterone would release the inhibitory effect on osteoclasts, resulting in release of calcium form the bone. Testosterone also binds to osteoblast receptors, stimulating the bone to form new bone, which moves calcium into bone. A drop in testosterone would also result in a drop in bone formation. The combined result would be a rise in extracellular calcium levels.

Testosterone levels can vary widely among individuals, with adult male plasma testosterone levels ranging between 3-10 ng/ml (10-35 nmol/L). In prepubertal boys, testosterone ranges from 0.2 to 0.7 nmol/L (0.05 to 0.2 ng/ml), and at the start of puberty, nocturnal gonadotropin surges result in nocturnal testosterone surges. The initially low daytime levels of testosterone gradually increase as puberty progresses and reach adult levels at about age 17. In young adult men, plasma testosterone is 30% higher in the morning than in the evening. Testosterone levels in adults are also subject to fluctuations. Testosterone levels rise in winners of competitive contests and decrease in losers. Studies have shown that testosterone surges after watching a pornographic film, with a median increase of 100% in men and 80% in women, with much higher surges in certain individuals. Studies have shown that although alcohol eventually reduces testosterone levels, some individuals may transiently experience a surge in testosterone after alcohol consumption. Less sleep has also been correlated to reduced testosterone levels. Studies have shown seasonality with the highest testosterone levels occurring in June-July and minimum levels during winter-early spring. In males, bioavailable testosterone levels decline around 1.2% per year after age 40.

A transient drop in testosterone levels would result in an increase in extracellular calcium levels which in turn would follow the same pathogenesis pathways presented above, namely neuronal "hypersensitization" via 1) neuronal membrane depolarization, 2) upregulated neurotransmitter release at synapses, and 3) PTP mechanisms and muscular "hypercontractility" via 1) enhanced acetylcholine release at the neuromuscular junction and 2) directly enhanced muscle contractility via the enhanced inrush of $Ca^{2+}$ into the sarcoplasmic reticulum, enhanced tropomyosin block removal, enhanced actin-myosin cross-bridging. Conversely, a rise in testosterone levels would result in a reduction in extracellular calcium levels and "desensitization" of nerves.

Prostaglandins, Bone, and Extracellular Calcium Levels

Increases in prostaglandin levels result in increased extracellular calcium levels and follow the same pathogenesis as presented above for drops in estrogen or testosterone levels.

Prostaglandins exhibit PTH-like (parathyroid hormone) effects that result in calcium mobilization from the bone (*Therapy of Renal Diseases and Related Disorders, Second Edition*, Kluwer Academic Publishers, 1991, page 98) and prostaglandin synthetase inhibitors are a textbook method for reducing calcium levels in management of hypercalcemia (*Therapy of Renal Diseases and Related Disorders, Second Edition*, Kluwer Academic Publishers, 1991, page 98).

As an example, prostaglandin E (PGE2) is a potent stimulator of bone resorption (Miyaura et. al., " . . . *Prostaglandin E2-mediated Bone Resorption Associated with Inflammation*", *J. Exp. Med.*, Vol. 197, No. 10, May 19, 2003 1303-1310). The production of PGE2 by osteoblasts is regulated by several cytokines, including interleukins IL-1 and IL-6, which upregulate osteoblast expression of cyclooxygenase 2 (COX-2) and membrane bound PGE2 synthase (mPGES), both of which are used in the synthesis of PGE2 from arachidonic acid. IL-1 and IL-6 are produced as part of an inflammatory response (IL-1 by monocytes, macrophages, and dendritic cells and IL-6 by T2 lymphocytes and monocytes/macrophages). PGE2 in turn acts as a potent stimulator of bone resorption and inflammatory bone loss is accompanied by osteoclast formation, however the mechanisms are not yet fully understood.

The prostaglandin induced bone resorption would increase extracellular calcium levels and would in turn follow the same pathogenesis pathways presented above, namely neuronal "hypersensitization" via 1) neuronal membrane depolarization, 2) upregulated neurotransmitter release at synapses, and 3) PTP mechanisms and muscular "hypercontractility" via 1) enhanced neurotransmitter release at the neuromuscular junction and 2) directly enhanced muscle contractility via the enhanced inrush of $Ca^{2+}$ into the sarcoplasmic reticulum, enhanced tropomyosin block removal, enhanced actin-myosin cross-bridging (with eventual muscle weakness in the case of chronic neurotransmitter depletion).

The above prostaglandin pathways are consistent with certain clinical observations. As an example, ingestion of certain foods of substances can sometimes act as a "migraine trigger". In context of the above pathogenesis, exposure to substances that result in antigen/allergen activation of immune system cells, with resulting PGE2 synthesis upregulation as described above, would potentially function as "triggers" in certain individuals (via the resulting spike in Ca2+ levels). People with low seizure thresholds would also be more susceptible to these "triggers".

As another example, prostaglandins are released during menstruation due to destruction of the endometrial cells and studies have shown prostaglandin levels are higher in women with primary dysmenorrhea (severe menstrual cramping). Women with primary dysmenorrhea have increased contractility and increased frequency of contractions of the uterine muscle. These are all consistent with the underlying etiology disclosed related to prostagandin-osteoclast-$Ca^{2+}$ modulated neural and muscular "hypercontractility". Prostaglandin inhibitors, such as NSAIDs, can provide relief, which is also consistent with the pathogenesis presented, as NSAIDs would reduce prostaglandin levels, and hence reduce the elevated extracellular calcium levels and their downstream events.

As another example, alcohol's intoxicating effects are related to enhanced GABA neurotransmission in the brain, however alcohol intoxication also results in cell destruction (which in turn results in elevated prostaglandin levels) and a reduction in testosterone levels (albeit after a brief rise in certain subjects), for a "double whammy" of elevated $Ca^{2+}$ levels, the predicted effects of which are consistent with a hangover headache (e.g. hypersensitivity to sound).

Vitamin D, Bone, and Extracellular Calcium Levels

The active form of Vitamin D ($1.25[OH]_2D$), also known as calcitriol or DHCC or 1.25 OHD or 1.25D, promotes osteoclast activity by binding to vitamin D receptors (VDR) in osteoblasts and upregulating expression of RANKL. Vitamin D also activates absorption of calcium in the intestine and reabsorption of calcium by the kidney. Accordingly, the active form of vitamin D has a "triple whammy" effect on elevating extracellular calcium levels. The resulting elevation in extracellular calcium levels from calcitriol would result the nerve and muscle "hypersensitization" by the pathogenesis as previously disclosed.

Exposure to sunlight (UVB) would have a material effect on vitamin D levels, and hence extracellular calcium levels. Normally, around 90% of the human requirement for vitamin D comes from exposure to sun. Skin is unique in that it is capable of manufacturing biologically active 1.25 D in the presence of UVB light from start to finish (unlike the "need regulated" conversion by the kidney). Full body exposure to UVB for 20 minutes in midday summer sun, in fair skinned people, can result in 10,000 IU of vitamin D being synthesized by the skin (25 times the recommended daily allowance of 400 IU). The effectively unregulated production of active 1.25 D by the skin would boost $Ca^{2+}$ levels by the three pathways previously disclosed (i.e. increased release of calcium from bone, increased reabsorption of calcium by the kidneys, and increased absorption of calcium from the intestines) and the biological effect would last for a period of time commensurate with the amount of 1.25D synthesized and its half life (3-6 hours).

The other source of vitamin D synthesis is inside the body. The conversion of the inactive form of Vitamin D to the active form 1.25 D (calcitriol) involves two hydroxylations (addition of OH groups). The first hydroxylation is at the C-25 position and occurs in the liver through a cytochrome P-450 dependent enzyme and the second hydroxylation is at the C-1 position and occurs in the kidney. Parathyroid hormone (PTH) stimulates 1-hydroxylase and inhibits 25-hydroxylase. Calcitriol represses synthesis of 1-hydroxylase and enhances synthesis of 25-hydroxylase. Under normal conditions, low serum $Ca^{2+}$ levels increase PTH synthesis, which in turn increase conversion of vitamin D to its active form, which in turn elevates extracellular calcium levels by the three pathways disclosed above (i.e. increased release of calcium from bone, increased reabsorption of calcium by the kidneys, and increased absorption of calcium from the intestines). Elevated levels of the active form of vitamin D function to repress synthesis of 1-hydroxylase, which in turn functions to repress further conversion of vitamin D to its active form.

Vitamin D levels can vary widely. The reference range for plasma levels of 25 D is from 8-80 ng/ml (20-200 nmol/L) and plasma levels of 1.25 D range from 16-65 pg/ml (40-160 pmol/L).

Vitamin D intoxication is a cause of hypercalcemia. Abnormalities in any of the vitamin D synthesis, activation, or feedback loops, or impaired liver or kidney function, can result in abnormalities in 1.25 D (calcitriol) levels, which in turn would lead to abnormalities in management of extracellular $Ca^{2+}$ levels, which in turn would result in abnormalities in nerve and muscular function via the novel pathogenesis pathways disclosed in present application. The abnormality would depend on the defect, and defects resulting in elevated $Ca^{2+}$ levels would result in "hypersensitization" of nerves and muscles and defects resulting in low $Ca^{2+}$ levels would work in reverse, resulting in "hyposensitization".

Drugs that interact with vitamin D synthesis, activation or feedback loops would also result in similar abnormalities that work their way through the novel pathogenesis presented in present application, in a manner that alters nerve and muscle function. Examples of such drugs include phenytoin, phenobarbital, carbamazepine, and primidone.

It should be noted that blood levels of 1.25 D are the relevant measure to be used for purposes of present invention, and not the commonly used 25 D measurements. Adequate or elevated levels of 25 D do not mean adequate or elevated levels of 1.25 D, and elevated levels of 25 D may be accompanied by inadequate 1.25 D levels (i.e. inadequate conversion of 25 D to the active form).

Other Compounds, Bone, and Extracellular Calcium Levels

The above endocrines are likely the primary ones involved in the majority of headaches, migraines, and seizures, in part because of the potential for large, abrupt changes in their levels. However, numerous other endocrines and compounds can also alter extracellular calcium levels. Examples include growth hormone (GH), insulin like growth factor (IGF), bone morphogenic protein (BMP), other androgens, IL-1, IL-6, etc. . . . hypercalcemia inducers such as vitamin A intoxication, aluminum intoxication, prolonged immobilization, thyroid/parathyroid abnormalities, adrenocortical insufficiency, malignant neoplasms, ingestion of thiazide diuretics, ingestion of lithium, etc. . .

TABLE 1

Endocrine Changes and Bone Microenvironment Effect

| Compound | Effect |
|---|---|
| decrease estrogen | increases extracellular calcium |
| decrease testosterone | increases extracellular calcium |
| increase prostaglandins | increases extracellular calcium |
| increase Vitamin D (1, 25D) | increases extracellular calcium |
| decrease growth hormones (GH, IGF, BMP) | increases extracellular calcium |
| increase parathyroid hormone (PTH) | increases extracellular calcium |

TABLE 1-continued

Endocrine Changes and Bone Microenvironment Effect

| Compound | Effect |
|---|---|
| decrease calcitonin | increases extracellular calcium |
| increase Vitamin A/Retinoids | increases extracellular calcium |
| increase Lithium | increases extracellular calcium |

Comparison of Pathogenesis Presented with Prior Art Treatment Methods

The bone microenvironment mediated migraine and seizure etiology and the pathogenesis of hypersensitization of nerves and muscles from the transiently elevated extracellular calcium levels, disclosed in this application, are novel over prior art.

In contrast, prior art has various theories about migraines as previously disclosed, and readily admits it cannot explain 70% of recurring seizures.

The latest explanation of migraines focuses on cerebral nerves and blood vessels. As summarized by the Scientific American: "Scientists thought for years that migraines were caused by the contraction and expansion of blood vessels in the head. Now many believe that nerve tissue is the primary culprit. Studies . . . using the imaging technique positron emission tomography (PET) showed that the attacks seem to arise when nerves deep within the brain stem, the lower part of the brain that abuts the spinal cord, became overstimulated." (Witte F, "*The Madness of Migraine*", Scientific American Mind, December 2006/January 2007, pages 39-43).

Numerous nerves sprout from the brain stem, including fibers of the massive trigeminal nerve. The Scientific American article continues that: "When the endings of the trigeminal nerve become overwrought, because of genetic or environmental factors, or both, they release large amounts of chemicals called neuropeptide . . . . This release spawns inflammation in nearby blood vessels and thereby excites pain receptors of the trigeminal nerve, whose signals reach the brain stem . . . . At the brain stem, pain-processing centers can become sensitized or overloaded and start firing spontaneously, producing the pain of migraine." The article continues on to state that inhibiting the release of the neuropeptides is now considered central to the physiology of migraines.

Although the etiology of endocrine modulated changes in the bone microenvironment/elevated calcium levels presented may appear distinctly different from the prior art trigeminal nerve etiology, the hypersensitization of the trigeminal nerve is actually predicted under pathogenesis of present invention. The primary difference is that present invention traces the true etiology several steps further back to the bone microenvironment, which not only explains the numerous disparate observations as previously discussed, but allows applicant to provide novel etiology based treatment methods.

In addition to having previously explained the numerous clinical observations related to migraines in light of the elevated calcium pathogenesis presented, it is also possible to view drugs known to provide therapeutic benefit, for both migraines and seizures, in context of the novel pathogenesis presented.

Prior Art Migraine Treatments:

Nonsteroidal Anti-Inflammatory Drugs (NSAIDs): NSAIDs used for symptomatic relief include excedrin migraine, aleve, vioxx, celebrex, advil, motrin IB, nuprin, actron, orudis KT, aspirin (bayer, bufferin, ecotrin), and tylenol. NSAIDs used for preventative therapy include cataflam, lodine, ansaid, genpril, haltran, ibifon, ibren, ibu, ibuprin, ibuprohm, ibu-tab, medipren, motrin, q-profen, toradol, meclomen, aleve, and anaprox.

Under pathogenesis of present invention, NSAIDs would provide relief in patients where prostaglandins were responsible, in whole or in part, for the elevation in extracellular calcium levels. NSAIDs inhibit prostaglandin synthesis. Prostaglandins are potent stimulators of bone resorption and as such would result in the elevation in extracellular calcium levels, which in turn would result in nerve and muscle hypersensitization by mechanism disclosed under pathogenesis of present invention. Accordingly, prostaglandin synthesis inhibitors would function to reduce extracellular calcium levels where prostaglandins were contributing, in whole or in part, to rising extracellular calcium levels. Additionally, the standard benefits of reduced inflammation/reduced pain would also apply (e.g. reduced fluid pressure on mechanical stretch or pressure sensors, such as somatosensory and auditory receptors, and hence less potential for initiating pain signals at the front end of sensory nerve pathways).

Studies of migraineurs urine in the 1960s revealed serotonin abnormalities and research suggested boosting serotonin levels could decrease symptoms ("*Migraines and Serotonin Receptors*", Society for Neuroscience, February 1998).

Selective Serotonin Reuptake Inhibitors (SSRI): SSRIs used to treat migraines include fluoxetine (Prozac), nefazodone (Serzone), paroxetine (Paxil) sertraline (Zoloft), and venlafaxine (Effexor). Serotonin is a neurotransmitter that is used widely including in the spinal cord, the brain, by the trigeminal nerve, and in blood vessels that service the head as well as other parts of the body such as the heart. SSRIs block serotonin reuptake pumps.

Under pathogenesis of present invention, SSRIs would function to counteract calcium related nerve hypersensitization via serotonin autoreceptor pathways. Autoreceptors provide negative feedback to synthesis/release of neurotransmitter, based on levels of neurotransmitter present at the gap junction. SSRIs block serotonin reuptake pumps, blocked reuptake pumps result in elevated levels of serotonin at the gap junction, elevated levels of serotonin in turn result in upregulated autoreceptor activation, upregulated autoreceptor activation results in downregulation of synthesis/release of serotonin by the presynaptic nerve cell. SSRIs' downregulation of serotonin production/release by the presynaptic cell would work to counteract the upregulated serotonin release mediated by the elevated Ca2+ inrush under pathogenesis of present invention. As such, the beneficial effect of SSRIs is consistent with the pathogenesis and pathways of present invention.

Serotonin Receptor Agonists/Triptans: For many people, triptans (serotonin receptor agonists) are effective in relieving the pain, nausea and sensitivity to light and sound that are associated with migraines. Sumatriptan (Imitrex) was the first drug specifically developed to treat migraines. Related medications include rizatriptan (Maxalt), naratriptan (Amerge, Naramig), zolmitriptan (Zomig), almotriptan (Axert, Almogran), frovatriptan (Frova, Migard) and eletriptan (Relpax).

Drugs such as sumatriptan target serotonin receptors located on both the trigeminal nerve and blood vessels that service the head. Sumatriptan binds to and activates these receptors. The working theory under prior art was that: "(1) Blood vessels have an intrinsic tone under normal conditions. (2) During a migraine attack, the blood vessels dilate. This "stretching" of the blood vessel walls may produce migraine symptoms. (3) Migraine pain also may stem from the release of peptides from the trigeminal nerve terminals, which project to the blood vessels. The peptides may alter pain thresholds. (4) Many researchers believe that sumatriptan and other related anti-migraine drugs under investigation counter one or both of these migraine contributors through their actions on specific serotonin receptors" ("*Migraines and Serotonin Receptors*", *Society for Neuroscience*, February 1998).

Under pathogenesis of present invention, elevated extracellular Ca2+ levels would result in hypersensitization of nerves and muscles, resulting in initial hyper constriction of blood vessels, followed by eventual dilation of blood vessels from neurotransmitter over release/depletion (as previously disclosed). Serotonin analogs would function by both autoreceptor pathways (as disclosed above for SSRIs) and compensatory pathways to prevent migraines under pathogenesis of present invention. First, serotonin receptor agonists would result in larger serotonin concentrations in the synaptic gap, which would upregulate autoreceptors that downregulate synthesis/release of neurotransmitters by the presynaptic nerve cell. This would counteract the elevated Ca2+ mediated "over release" of neurotransmitter (i.e. thus reduce sensory hypersensitivity, delay/prevent neurotransmitter depletion). Second, serotonin receptor agonists would directly provide a low level of post synaptic stimulation, reducing the amount of indigenously produced serotonin required for continued nerve transmission (e.g. thus maintain normal blood vessel tone).

CGRP Receptor Antagonists: CGRP is one of the neuropeptides released by the trigeminal nerve. "CGRP from trigeminal nerves is now thought to play a central role in the underlying pathophysiology of migraine" (Durham P L, "*CGRP—Receptor Antagonists—A Fresh Approach to Migraine Therapy?*", *New England Journal of Medicine* 350; 11, Mar. 11, 2004). Drugs such as Merck's MK-0947, which recently demonstrated efficacy in Phase III clinical trials, function as CGRP receptor antagonists. The New England Journal of Medicine (NEJM) article discloses that serum levels of CGRP are elevated in patients with migraines and cluster headaches. The NEJM article discloses that CGRP released from the trigeminal nerve 1) binds to CGRP receptors on meningeal mast cells triggering release of inflammatory agents, 2) binds to CGRP receptors on blood vessels endothelial cells resulting in vasodilation, and 3) functions as a trigeminal nerve synaptic gap neurotransmitter and is involved in the transmission of painful stimuli.

CGRP antagonists, or any other method of counteracting the hypersensitization/hyperactivity of nerves, including the massive trigeminal nerve, should provide therapeutic benefit and is consistent with pathogenesis of present invention.

Blood Pressure Medications: High blood pressure medications such as beta blockers (which slow heart rate an reduce blood pressure) and calcium antagonists (which ease blood flow) have shown efficacy against migraines. Beta blockers include tenormin, tenoretic, lopressor, corgard inderal, and blocadren. Calcium channel blockers include cardizem, cardene, procardia, nimotop, calan, isoptin, and verelan.

Under pathogenesis of present invention, a drug that drops blood pressure would work to offset elevated calcium levels. Hypotension alters renal function in the Loop of Henle, which results in higher concentrations of Na+ in the blood, and hence higher water concentration in the blood. Fluid expansion is one method of managing hypercalcemia. More Ca2+ would be drawn into the collecting ducts by osmotic potential, and excreted in the urine, lowering serum calcium levels.

Accordingly, the therapeutic effect of hypotensive drugs is consistent with the pathogenesis of present invention, and the therapeutic benefit would be predicted under the pathogenesis of present invention as hypotensives would reduce calcium levels.

Tricyclic Anti-depressants: Tricyclic antidepressants that are used treat migraines include amitriptyline (Elavil), desipramine (Norpramin), doxepin (Sinequan), imipramine (Tofranil), and nortriptyline (Pamelor). They have multiple mechanisms of action, however, all inhibit reuptake of serotonin and/or norepinephrine (noradrenaline). Both mechanisms of action are consistent with providing relief under pathogenesis of present invention. Inhibiting reuptake of serotonin would function by the pathways as described above for SSRIs. Inhibiting norepinephrine reuptake enhances activation of pathways in the spinal cord that block pain from ascending to the brain. This would work to offset the extracellular Ca2+ mediated "hypersensitization" of sensory nerves that conduct pain under pathogenesis of present invention.

Prior Art Anti-Seizure/Anti-Migraine Treatments:

Anti-seizure medications used to also treat migraines include topiramate (Topamax), divalproex (Depakote), gabapentin (Neruontin), and verapamil (Covera).

The mechanism of action (MOA) varies somewhat between these drugs, however the various MOAs are all consistent with providing therapeutic benefit under pathogenesis of present invention. The MOAs counteract elevated Ca2+ effects via modulation of the neurotransmitter gamma-amino butyric acid (GABA), modulation of GABA receptors function, blocking voltage gated sodium channels, or some combination of the listed MOAs.

GABA is the main inhibitory neurotransmitter in the body. $GABA_A$ receptors are the most prevalent inhibitory receptor within the brain. Activation of $GABA_A$ receptors increases the frequency of opening of the associated chloride ion channels, hyperpolarizing the membrane of the associated neuron. $GABA_B$ receptors couple to potassium and calcium channels and activation of presynaptic $GABA_B$ receptors inhibits neurotransmitter release at most cortical synapses, at least in part because of inhibition of voltage-gated calcium channels (Wang and Lambert, "*GABAB Receptors Couple to Potassium and Calcium Channels . . .* " *Journal of Neurophysiology*, Vol. 83, No. 2. February 2000, pp. 1073-1078).

Topiramate (Topamax) blocks voltage gated sodium channels and augments activity of GABA (gamma-amino butyric acid) at certain $GABA_A$ receptors (per the topiramate full prescribing information). Both MOAs function to counteract the hypersensitization of nerves from the elevated extracellular Ca2+ levels under pathogenesis of present invention. The upregulation of $GABA_A$ receptor activity results in increased opening of the chloride ion channels and hyperpolarization of the nerve membrane, which functions to counteract the depolarization of the nerve membrane from the elevated Ca2+ levels (by the Nernst equation, as previously discussed). Topiramate's second MOA of blocking voltage gated sodium channels functions to antagonize signal transmission directly (as sodium influx into the nerve is required for signal propagation).

Divalproex/valproate/valproic acid (Depakene, Depakote) increases brain concentrations of GABA (per the divalproex full prescribing information). Activation of both GABA receptor types A and B would work to counteract the Ca2+ nerve hypersensitization. The $GABA_A$ related hyperpolarization would work to counteract the Ca2+ membrane depolarization. The $GABA_B$ related voltage gated calcium channel inhibition and downregulation of presynaptic neurotransmitter release would work to counteract the upregulation of presynaptic neurotransmitter release from the larger Ca2+ inrush through the voltage gated calcium channels under pathogenesis of present invention.

Gabapentin (Neurontin) prevents pain-related responses in several models of neuropathic pain and has high affinity binding to an auxiliary subunit of voltage-activated calcium channels in animal brain tissue (per the gabapentin full prescribing information). Inhibiting voltage gated calcium channels works to offset the excessive inrush of Ca2+ through the calcium channels under pathogenesis of present invention (similar to magnesium, a physiological calcium channel blocker, as previously disclosed).

Verapamil (Covera) is a calcium ion influx inhibitor (L-type calcium channel blocker or calcium channel antagonist) which selectively inhibits the transmembrane influx of ionic calcium into arterial smooth muscle (per the full prescribing information). Verapamil binding affinity increases when membrane potential is reduced and affinity also increases with increased frequency of depolarizing stimulus, both situations being consistent with (and predicted by) the pathogenesis of present invention.

Prior Art Anti Seizure Mediations:

In addition to the dual anti seizure, anti migraine treatments previously discussed (i.e. topiramate (Topamax), divalproex (Depakote), gabapentin (Neruontin), and verapamil (Covera), a more comprehensive discussion of prior art anti seizure medications (per WebMD, Epilepsy Health Center Reference collaboration with Cleveland Clinic, "*Epilepsy: Medications to Treat Seizures*", website printout of Jul. 13, 2008, provided under IDS) is provided below:

Benzodiazepines: Benzodiazepines produce a range of effects, including $GABA_A$ receptor activity upregulation and calcium channel blocking. Benzodiazepines bind to subunits on certain $GABA_A$ receptor. Once bound, the benzodiazepine ligand locks the $GABA_A$ receptor into a conformation in which it has a much higher affinity for the GABA neurotransmitter than otherwise. This increases the frequency of opening of the associated chloride ion channel and hyperpolarizing the membrane of the associated neuron. The anticonvulsant properties of benzodiazepines have been attributed to inhibition of post synaptic GABA responses and inhibition of sustained high frequency repetitive firing. Benzodiazepines have also been shown to act via micromolar benzodiazepine binding sites as Ca2+ channel blockers and significantly inhibited depolarization-sensitive calcium uptake in an experiment on rat brain cell components. Benzodiazepines used as anti-convulsants include lorazepam (Ativan, Temesta), diazepam (Valium), clonazepam (Klonopin), clorazepate (Tranxene, Tranxilium), midazolam (Dormicum, Flormidal, Versed, Hypnovel, Dormonid) and clobazam.

Carbamazepine: Carbamazepine and its derivatives are sodium channel blockers. After voltage-gated sodium channels open to start the action potential, they inactivate, essentially closing the channel. Carbamazepine stabilizes the inactivated state of sodium channels, meaning that fewer of these channels are available to open, making brain cells less excitable. Carbamazepine has been sold under the names Tegretol, Biston, Calepsin, Carbatrol, Epitol, Equetro, Finlepsin, Sirtal, Stazepine, Telesmin, Teril, Timonil, Trimonil, Epimaz, Carbama/Carbamaze, and Degranol.

Ethosuzimide (Zarontin, Emeside): The exact mechanism by which ethosuzimide exerts its anti-convulsant effects have not been definitively established, however existing studies focus on T-type Ca2+ channel blocking as the underlying MOA.

Felbamate (Felbatol): The drug's MOA is not known.

Tiagabine (Gabitril): The drug appears to operate as a selective GABA reuptake inhibitor.

Levetiracetam (Keppra): The mechanism of action is unknown. The drug is not chemically related to other anticonvulsants and does not appear to act through the traditional mechanisms of neurotransmitter modulation. Animal studies suggest that levetiracetam may act by preventing hypersynchronization of epileptiform burst firing, producing an inhibition of the spread of seizure activity. The recent discovery of a specific binding site for levetiracetam in the brain may lead to more information in the future.

Lamotrigine (Lamictal): Lamotrigine inhibits voltage-sensitive sodium channels, thereby stabilizing neuronal membranes and consequently modulating presynaptic transmitter release.

Pregabalin (Lyrica): Pregabalin was designed as a more potent successor to gabapentin and like gabapentin, pregabalin binds to the α2δ (alpha2delta) subunit of the voltage-dependent calcium channel in the central nervous system. This reduces calcium influx into the nerve terminals and decreases the release of neurotransmitters.

Phenytoin (Dilantin, Phenytek): In chemical structure, phenytoin is related to the barbiturates. The mechanism of action is not definitely known, but extensive research strongly suggests that its main mechanism is to block frequency-, use- and voltage-dependent neuronal sodium channels, and therefore limit repetitive firing of action potentials.

Oxcarbazepine (Trileptal, Trexapin): Oxcarbazepine is structurally a derivative of carbamazepine. It is thought to have the same mechanism as carbamazepine—sodium channel inhibition (presumably, the main mechanism of action).

Zonisamide (Zonegran, Excegran): Zonisamide is used to treat both migraines and epilepsy. The exact mechanism of action is not known, however, it has been suggested that zonisamide raises the seizure threshold through action at sodium and calcium channels, stabilizing neuronal membranes and suppressing neuronal hypersynchronization.

In summary, all prior art anti-seizure medications work by reducing the ability of nerves to conduct electrical impulses. Compositions of present invention provide a novel, multifaceted, etiology based approach, inhibiting the bone microenvironment release of the Ca2+, which inhibits propagation of signals along membranes, downregulates presynaptic neurotransmitter release, and downregulates propagation of signals across muscles such as those found in cerebral blood vessels. The method of present invention would also enhance the efficacy of prior art's more single faceted, symptom based approaches, such as sodium channel blockers, calcium channel blockers, GABA upregulators, GABA receptor function upregulators, selective serotonin reuptake inhibitors, serotonin agonists, and other approaches for inhibiting nerve signal propagation in selected areas of the brian.

Combining the "low seizure threshold" concept disclosed under prior art, with disclosures of present invention, would provide a novel approach to managing seizures. Modulating the bone microenvironment to reduce extracellular calcium levels would raise the threshold for seizures, which would work to offset the low threshold for seizures as disclosed under prior art. A high threshold (hyperpolarized or "desensitized" nerves) means fewer seizures and less severe seizures, and potentially no seizures at all. A high threshold for muscle activation would mean less severe muscle contractions associated with seizures.

Applicability to Migraines and Seizures:

Although the compositions and methods of present invention modulate the bone microenvironment to modulate extracellular Ca2+ levels, and would work best when the underlying etiology of the migraine or seizure was related to a bone microenvironment mediated extracellular Ca2+ elevations, present invention would still work even if this was not the specific etiology for a given type of migraine or seizure.

Just as the above dual anti-seizure/anti-migraine medications provide therapeutic benefit to both conditions by attenuating nerve transmission pathways, so would therapeutics of present invention.

Dropping extracellular Ca2+ levels would serve to attenuate nerve signal transmission. This can be seen by going in reverse of the pathogenesis pathways presented.

First, lowering Ca2+ would result in hyperpolarization of nerves, per the Nernst equation example previously presented. Using the example previously presented, except going in reverse from a 2 mM to 1 mM extracellular $Ca^{2+}$ concentration, would make the resting membrane potential more negative by 6 mV, raising the resting membrane potential from −79 mV to −85 mV, which in turn would increase the amount of input stimulus required to trigger a nerve impulse from 9 mV to 15 mV.

Second, lowering Ca2+ would result in lower Ca2+ inrush through the pre synaptic voltage gated calcium channels and hence lower neurotransmitter release. Once again, using the previous example except going in reverse, reducing extracellular $Ca^{2+}$ concentration from 2 mM to 1 mM would not only cut the amount of $Ca^{2+}$ available for inrush in half, but would drop the driving force of the inrush (i.e. the concentration gradient) by almost 40% (from a 12,500 times greater concentration on the outside to a 7,672 times greater concentration on the outside). Both would function to reduce the amount of neurotransmitter released from the presynaptic vesicles.

Likewise, going in reverse down the neuromuscular pathways previously presented, lowering extracellular calcium concentrations would reduce the transmembrane influx of ionic calcium into arterial smooth muscle, as well as other muscles.

Because the mechanism of action (MOA) of present invention is novel and different than those currently employed to treat migraines or seizures, the methods of present invention may also be used to potentiate or enhance the effects of the prior art treatment methods listed above.

Calcium Levels and Seizures

As methods of present invention modulate the bone microenvironment in order to modulate extracellular calcium levels, a brief background of calcium, as it relates to seizures, is presented below.

As previously mentioned, the average adult human body contains 1.3 kg of calcium of which 99% is contained in bones, 1% in cells of soft tissue, and 0.15% in the extracellular fluid. Normal serum plasma levels of calcium range from 8.0 to 10.8 mg/dl (2.2 to 2.7 mmol/L) with approximately 50% being free ionized calcium. Because of the large reservoir of bone calcium (i.e. 99%), versus the extremely small extracellular amount (i.e. 0.15%), perturbations resulting in the release of reservoired bone calcium have the potential for profound transient effects on extracellular calcium concentrations.

Both Hypercalcemia and Hypocalcemia can result in seizures. In hypercalcemia, EEG changes appear when serum calcium levels reach 13 mg/dl and above 16 mg/dl grand mal attacks (now referred to as tonic-clonic seizures, a type of generalized seizure affecting the entire brain and most commonly associated with epilepsy) and massive spike activity over the right and left occipital lobes are often observed (*Electroencephalography*, Niedermeyer and Da Silva, p. 445). In hypocalcemia, epileptic manifestations develop at calcium levels of 5-6 mg/dl (*Electroencephalography*, Niedermeyer and Da Silva, p. 444).

The mechanisms underlying seizures from hypercalcemia can be explained by the nerve hypersensitization pathogenesis presented in this application. As previously disclosed, the elevation in extracellular calcium would result in 1) depolarization of nerve membranes by the Nernst equation, 2) upregulated calcium inrush via voltage gated calcium channels, which in turn results in upregulated presynaptic neurotransmitter release, and 3) PTP effects.

The mechanisms underlying seizures caused by hypocalcemia have not yet been fully defined. What is known is that hypocalcemia decreases the activation threshold of sodium channels. What is not known is how this happens. Studies have also provided evidence of interaction between serum hypocalcemia and respiratory alkalosis in tetany, a disorder of neuronal excitability associated with hypocalcemia (Edmondson J W et. al., "*Tetany:quantitative interrelationships between calcium and alkalosis*", Am. J. Physiol, April 1975; 228(4):1082-6). In the study, tetany occurred in less than 50% of dogs made either hypocalcemic or made alkalotic, however, hypocalcemia combined with hypocapnic alkalosis always produced tetany.

It should be noted that serum calcium levels may not accurately reflect extracellular calcium. There is a clear time lag on the order of hours for equilibrium of calcium ions across the blood brain barrier. Furthermore, it should also be noted that neuronal excitability (i.e. "seizure threshold") for a given serum level of calcium may vary widely between individuals. Patients with familial hemiplegic migraine have been shown to have dysfunctional sodium channels that tend to stay open too long (*Science Daily*, Jul. 1, 2008 synopsis of Vanderbilt University study conducted by Dr. Alfred George), which would function to heighten neuronal excitability at a given level of elevated calcium versus patients not possessing the mutation. Likewise, people with a genetically lower or higher population density of sodium or calcium channels than "normal" would also respond differently to a given calcium level.

Although the methods of present invention can be used as a stand alone treatment option, the best use would likely be concurrent with the numerous prior art methods previously listed, in order to enhance the efficacy of the prior art therapeutics. This would allow for more moderate modulations of the bone microenvironment, which in turn would also provide a much greater margin of safety.

Seizures and Pathogenesis of Present Invention

According to the Epilepsy Foundation, the "Seizure Threshold" concept holds that "everyone has a certain balance (probably genetically determined) between excitatory and inhibitory forces in the brain" and "if there is a consistently higher level of the excitatory neurotransmitters, or too few inhibitory ones, the likelihood of a seizure—an uncontrolled firing of the neurons in the brain—is increased. Some of the newer medications relate directly to this process and are designed to increase the level of inhibitory neurotransmitters, especially gamma-aminobutyric acid (GABA), or to decrease the amount of the excitatory ones, such as glutamate."(http://www.epilepsyfoundation.org/about/science/index.cfm, provided under IDS).

Studies have found that "Epilepsy and its therapies—older or modern—are both risk factors for low bone density" (Short R, *"Effect of anti epileptic drugs on bone density in ambulatory patients"*, Neurology 2002;58:1348-1350). The study found that traditional enzyme inducing anti epileptic drugs (e.g. carbamazepine, phenytoin, phenobarbital, primidone) had more bone loss than non enzyme inducing drugs (e.g. valproic acid, lamotrigine, clonazepam, gabapentin, topamirate, and ethosuximide), however both were risk factors for bone loss. This points to epilepsy, and its treatments, as involving the bone microenvironment in a manner that is consistent with pathogenesis of present invention.

The severity of the bone loss is summarized well by Elliott et. al.: "Anti epileptic drugs are known to cause bone loss. People with epilepsy have twice the fracture rate of non epilepsy populations." "Studies have demonstrated that bone loss can occur after as little as 2 years of anti epileptic drug (AED) exposure . . . and . . . people with epilepsy who take enzyme inducing AEDs are prone to significant loss of bone mass, based on current World Health Organization guidelines. Only 42% had normal bone density compared with 84% expected in the general population." (Elliott J et. al., *"Osteoprotective Knowledge in a Multiethnic Epilepsy Population"*, J. Neurosci. Nurs., 2008;40(1):14-24).

Enzyme inducing anti epileptic drugs (EIAEDs) have the side effect of interfering with vitamin D synthesis and thus reducing bone density over time.

Under pathogenesis of present invention, the reduction of vitamin D synthesis capability may likely be the primary mechanism of action in preventing seizures, or at a minimum play a major contributory role, in addition to the attenuation of nerve transmission by the various "primary" MOAs stated for the various drugs currently in use (i.e. sodium channel blocking, calcium channel blocking, GABA upregulation etc. . . . ).

As previously disclosed, vitamin D is an extremely potent modulator for calcium levels, primarily because it targets all 3 potential sources/destinations of calcium. Vitamin D 1) increases absorption of calcium from the intestines, 2) inhibits excretion of calcium by the urine, and 3) increases release of calcium from bone. All 3 sources result in escalation of extracellular calcium levels. Conversely, a reduction or deficiency of of vitamin D would drop calcium levels by all 3 MOAs in reverse: 1) decreasing absorption of calcium from the intestines, 2) increasing excretion of calcium in the urine, and 3) decreasing release of calcium from bone. Accordingly, inhibiting Vitamin D synthesis would drop Ca2+ levels, which would raise threshold potential (i.e. hyperpolarize or "desensitize" nerves and muscles) and reduce the likelihood of seizures, as disclosed under novel pathogenesis of present invention.

Just as vitamin D intoxication is a known cause of hypercalcemia, elevations in vitamin D levels (from exposure to sunlight, food intake, or both) can mechanistically cause enough of a rise in calcium (and hence neuronal hypersensitization via depolarization under pathogenesis of present invention) to trigger seizure in patients with low "seizure thresholds" (particularly when also combined with other simultaneous endocrine changes such as drops in estrogen or testosterone levels or a rise in prostaglandins).

Clinical corroboration for this exists from various unrelated studies. Carbamazepine is a sodium channel blocker that also interferes with vitamin D synthesis (hence also inhibiting the potential for any vitamin D related calcium spikes). Remacemide is a glutamate (major excitatory neurotransmitter in the brain) antagonist and one of the "newer generation" drugs designed not to interfere with vitamin D synthesis. In a comparative study of 449 patients, carbamazepine was shown to be significantly more effective than remacemide, with a median time to first seizure of 306 days for carbamazepine versus 112 days for remacemide (Brodie M J et. al. *"Efficacy and safety of Remacemide versus Carbamazepine . . . "*, Epilepsy & Behavior, Volume 3, Number 2, April 2002, PP. 140-146). This is consistent with the additional benefit of vitamin D synthesis suppression, versus only inhibition of neuronal transmission activity.

The effect of carbamazepine on vitamin D synthesis suppression can be seen from another study. Mintzer et. al. conducted a study that addressed the "concerns about the potential for chronic side effects with use of anti epileptic drugs" (Mintzer S et. al., *"Vitamin D levels and Bone Turnover in Epilepsy Patients Taking Carbamazepine or Oxcarbazepine"*, Epilepsia, 47(3):510-515, 2006). The study included measurements of serum calcium, 25-OHD, parathyroid hormone (PTH), and markers of bone resorption including osteocalcin (OCLN) and bone alkaline phosphatase (BAP) for both carbamazepine (CBZ) and Oxcarbazepine (OXC). The prevailing theory is that "inducers of hepatic cytochrome P450 system (CYP450) promote the metabolism of 25-hydroxyvitamin D (25-OHD) to less biologically active analogues, resulting in decreased bone mineralization, decreased intestinal calcium absorption, increased calcium mobilization from the skeleton" and the study sought to gain insight if the newer generation limited enzyme inducer OXC would have lower side effects than CBZ, a potent broad-spectrum CYP450 inducer. The unfortunate aspect of the study was that it did not measure 1.25-OHD levels, the "active form" of vitamin D, which would have provided meaningful data for analytical purposes. Measurements of 25-OHD are ambiguous as they can be inversely related to 1.25-OHD (i.e. a high rate of 1.25-OHD synthesis would result in lower 25-OHD levels) just as 25-OHD levels can be proportionately related to 1.25 OHD levels (i.e. inadequate synthesis of the precursor would translate to inadequate synthesis of the active product).

The data from the Mintzer et. al. study is as follows:

TABLE 2

Mintzer et. al. Data

|  | Control | CBZ | OXC |
| --- | --- | --- | --- |
| Calcium (mg/dl) | 9.4 | 9.3 | 9.3 |
| 25-OHD (ng/ml) | 27.5 | 20.4 | 19.4 |
| PTH (pg/ml) | 45.7 | 55.6 | 55.6 |
| OCLN (ng/ml) | 2.4 | 3.6 | 2.8 |
| BAP (U/L) | 22.4 | 27.7 | 28.5 |
| Calcium Intake (mg) | 673 | 448 | 530 |
| Age | 31 | 35 | 41 |
| Gender (M/F) | 9/15 | 13/8 | 17/7 |

The data shows normal calcium levels across all 3 groups, however both AED groups have low 25-OHD levels, high PTH levels, and high levels of markers for bone turnover. This is indicative of PTH mediated release of bone calcium (via PTH's boosting of RANKL) to maintain serum calcium levels, as the lower vitamin D levels would result in less calcium absorbed from intestines and less calcium retained by kidneys. PTH also increases synthesis of 1 hydroxylase, which in turn would increase synthesis of 1.25OHD under normal circumstances, however this is presumably prevented by the AEDs (unfortunately the study did not measure 1.25-OHD levels, however the high PTH levels are consistent with a deficiency of 1.25-OHD).

Under pathogenesis of present invention, low 1.25 D synthesis would provide therapeutic benefit against transient extracellular hypercalcemia and hence nerve hypersensitization. Low 1.25 D levels not only prevent the release of calcium form bone but reduce intestinal absorption and increase urinary excretion of calcium. Under the above scenario, the high PTH would release calcium from bones plus the low vitamin D levels would inhibit any potential "hypercalcemic spikes" as they would boost excretion of calcium in the urine and inhibit entry of new calcium from the intestines. Accordingly, under pathogenesis of present invention, prior art's "undesirable side effect" is effectively a major source of the therapeutic benefit, however at the expense of long term bone loss.

In contrast, treatment methods of present invention not only target the underlying etiology (versus just attenuating transmission of nerve impulses as under prior art) but do so in a manner that increases or conserves bone mass (versus prior art's methods that result in bone loss). Treatment methods of present invention would allow newer generation non enzyme inducing treatments like remacemide to reap the same dual benefits (calcium level downregulation+remacemide's own MOA) so as to put them on a level playing field with enzyme inducing drug's relative to efficacy, and without the commensurate bone loss. However, treatment methods of present invention would work best when they directly address an underlying etiology that involves calcium escalations.

As an example, 78% of women with refractory epilepsy reported that most of their seizures occurred near the time of and were exacerbated by menstruation (Duncan S et. al., "*How common is catamenial epilepsy*", Epilepsia, September-October 1993; 34(5):827-31). As previously disclosed, menstruation involves a precipitous drop in estrogen levels and transient spike in extracellular calcium levels from bone resorption, which in turn would hypersensitize nerves. As previously disclosed, prostaglandins are also released during menstruation due to destruction of the endometrial cells, which also release calcium from bone and exacerbate the hypersensitization of nerves. As methods of present invention target bone microenvironment to prevent release of the calcium, they would directly counteract the underlying etiology.

As another example, boys often start experiencing seizures during puberty. As previously disclosed, puberty has nightly testosterone spikes followed by precipitous daily drops (hence daytime Ca2+ spikes). When combined with a day on the beach (Vitamin D spike and hence Ca2+ spike) and/or sunburn (prostaglandin spike and hence Ca2+ spike) dangerous neuronal hypersensitization and seizure risk can be expected. Methods of present invention would directly target the bone microenvironment to prevent the above from occurring.

Additionally, conditions and situations that could potentially exacerbate or contribute to $Ca^{2+}$ spikes/levels resulting from changes in endocrine levels should also be reconsidered in light of pathogenesis of present invention (e.g. lithium ingestion, ingestion of thiazide diuretics, prolonged immobilization, thyroid or parathyroid abnormalities, adrenocortical insufficiency, magnesium deficiency, etc. . . . ).

Methods of Present Invention

In general, methods of present invention employ a simple philosophy: Targeting the underlying etiology is best, targeting the earliest downstream event(s) in the pathway is second best, and targeting further downstream events is least desirable. Current invention proposes an etiology based treatment approach.

Accordingly, present invention proposes to modulate the bone microenvironment, via modulation of osteoclast activity, osteoblast activity, or any combination of the two, in order to modulate the extracellular $Ca^{2+}$ levels, to counteract or "temper" the release rate of calcium stored in bone, and its subsequent neural and muscular effects, in conditions where endocrine oscillations (e.g. drops in estrogen levels, drops in testosterone levels, increases in prostaglandin levels, increases in vitamin D levels, etc. . . . ) are contributing, in whole or in part, to the underlying etiology of the migraine or seizure condition.

Present invention also proposes to modulate the bone microenvironment, via modulation of osteoclast activity, osteoblast activity, or any combination of the two, in order to modulate the extracellular $Ca^{2+}$ levels in order to attenuate neural and muscular hypersensitivity or "hyper excitability" in conditions where endocrine oscillations are not part of the underlying etiology, or where the underlying etiology is not known.

Present invention also proposes to modulate the bone microenvironment for purposes of enhancing the efficacy or therapeutic benefit of prior art medications in use today, or to be developed in the future, for treatment of migraines or seizures.

Materials of Present Invention

Since methods of present invention are directed toward modulating the bone microenvironment to alter extracellular $Ca^{2+}$ levels, in order to alter neural and muscular hypersensitization, any suitable materials or methods that modulate osteoclast or osteoblast population density, modulate osteoclast or osteoblast activity or functionality, so as to decrease Ca2+ release from bone or increase Ca2+ strorage into bone, decrease $Ca^{2+}$ absorption from the intestines, or increase $Ca^{2+}$ excretion by the kidneys may be used.

As used in the specifications, and its related claims, the scope of invention is intended to encompass the use of any anti-osteoclast compound(s) or any pro-osteoblast compound Anti-osteoclast compounds are hereby defined as any substance, either currently known or to be discovered or developed in the future, that inhibits osteoclast mediated release of calcium from the bone. Pro-osteoblast compounds are hereby defined as any substance, either currently known or to be discovered or developed in the future, that promotes osteoblast mediated storage of calcium in bone.

Some representative examples of such materials include, but are not limited, to the following:

Calcitonin:

Calcitonin can be used to inhibit $Ca^{2+}$ release from bone via its inhibitory effects on osteoclasts. Calcitonin causes osteoclast to lose their ruffled border which causes a marked transient inhibition of the bone resorptive process. Calcitonin also causes increased excretion of calcium (and phosphate and sodium) by the kidneys and evidence exists that calcitonin also reduces absorption of calcium in the gastrointestinal tract. Calcitonin is available in injectable form (e.g. Calcimar from Rhone-Poulenc Rorer or Caltine from Ferring) or as a nasal spray from (e.g. Fortical from Upsher-Smith or Miacalcin from Novartis) and oral formulations are currently under development. Calcitonin salmon is typically used (because of its greater potency), however because of the potential for allergic reactions adequate precautions should be taken as outlined in the prescribing information. Injections of 4-8 IU/kg (IM or SubQ) drop serum calcium levels by 1-2 mg/dl in most patients. Nasal administration of 2 IU/kg of salmon calcitonin results in a peak reduction of around 5% after 30 minutes of administration with an overall reduction in serum calcium of around 3.2% as expressed as the net change in AUC over 8 hours. Newer nasal formulations of polyethylene glycol conjugated salmon calcitonin have been able to boost the peak serum level reduction to 13% with an overall AUC reduction of 11.9%. Nasal calcitonin-salmon sprays (Miacalcin from Novartis and Fortical from Upsher-Smith) deliver 200 IU per spray and contain sufficient mediation of around 30 such doses. They are also fairly safe, as both Miacalcin and Fortical were tested at single 1,600 unit doses, and doses of 800 IU per day for 3 days, without serious adverse events.

Estradiol:

Exogenous estrogen can be used to inhibit osteoclast activity and bone resorption by the "triple whammy" previously disclosed, inhibiting osteoclast activity by binding to osteoblasts and 1) increasing their output of OPG and 2) suppressing their RANKL production and 3) prolonging the lives of osteoblasts while simultaneously promoting osteoclast apoptosis. A study (Ginsburg et. al., "Half life of Estradiol in Postmenopausal Women", Gynecologic and Obstetric Investigation, 1998;45:4548) showed that a 0.10 mg estradiol transdermal patch for thirteen hours resulted in an escalation of serum estrogen levels from a baseline of 19 pg/ml to 112 pg/ml and the mean half life of estradiol after removal of a transdermal patch was 2.7 hours (which puts the terminal half life at around 9 hours). The 112 pg/ml (0.1 ng/ml) is around the baseline level of estrogen levels during menstruation and could be used to cushion the decline in estrogen by administration of the patch on days 26-28 of the menstrual cycle when the estrogen decline is steepest as shown if FIG. 1. The dose is low enough and for a short enough period of time that it should not materially interfere with any of the menstrual processes. Alternatively, the patch may also be cut in half to obtain a half dose (0.05 ng/ml) cushion factor. Estrogen is available in oral, injectable, and patch forms from numerous suppliers and include Estrace, Cenestin, Enjuvia, Femtrace, Gynodiol, Menest etc. . . . An estradiol patch is used in preferred embodiment of present invention (e.g. Climara from Bayer) because of the continuous estradiol delivery (hence constant osteoclast inhibition) and because of the short terminal half life after removal of the patch. Likewise, androgens, such as testosterone, also inhibit osteoclast activity, and could be substituted.

SERM:

Selective estrogen receptor modulators (SERMs) such as raloxifene hydrochloride (Eli Lilly's Evista), that bind competitively to estrogen receptors and have estrogen-like effects on osteoblasts/osteoclasts and decrease resorption of bone, but lack estrogen-like effects on uterine and breast tissue, are preferred for use in present invention. Eli Lilly's Evista comes in 60 mg tablets. A single dose elevates serum concentrations to 0.5 ng/mL for every mg/kg of dose and has a serum elimination half life of 28 hours. Multiple dose administration results in maximum serum concentrations of 136 ng/ml with a serum elimination half life of 32.5 hours.

Androgens:

When androgens such as testosterone bind to osteoblast receptors, the osteoblast is stimulated to form new bone (i.e. move calcium into bone). Testosterone also demonstrates osteoclast inhibition, both directly and by its aromatization into estrogen. Accordingly, administration of androgens such as testosterone, or administration of endocrine hormones that upregulate indigenous production of androgens (e.g. in males, luteinizing hormone, gonadotropin/luteinizing hormone releasing hormone), can be used to reduce extracellular calcium levels by moving calcium back into bone. Testosterone USP is natural testosterone that has been approved by the United States Pharmacopoeia and is available as a bulk chemical. Testosterone is well-absorbed from transdermal (topical) creams and gels. Dosage forms also include sublingual drops, buccal or sublingual troches or tablet triturates. These offer better alternatives to oral Testosterone USP tablets, because testosterone that is absorbed through the gastrointestinal tract passes directly into the blood vessels supplying the liver, where the drug is significantly inactivated. In the form known as Testosterone Cypionate, testosterone can be administered by intramuscular injection every 1-3 weeks. WatsonPharma's Androderm transdermal 2.5 mg or 5 mg testosterone patch provides a more convenient way to administer testosterone, and provides the ability to administer the testosterone over a desired time frame much more precisely (as will be discussed further in representative examples). Androderm patches can ramp up testosterone levels quickly (e.g. 349 ng/dl within 3 hours, 528 ng/dl within 6 hours, when applied to the back) and can be used for up to 24 hours. The testosterone has an elimination half life of 71 minutes, which would return testosterone to baseline levels in about 3-4 hours after removal of the patch. Testosterone also comes in non aromatizable forms (Oxandrin from Savient Pharmaceuticals). Non aromatizable testosterone would function primarily by promoting osteoblast activity whereas aromatizable forms would promote both osteoblast movement of calcium into bone and inhibit osteoclastic movement of calcium out of bone (via the testosterone that is aromatized into estrogen). Aromatizable testosterones are generally preferred for use in present invention. Selective androgen receptor modulators (SARMs) currently under development may be steroidal (such as 7-Methyl-Nortestosterone or "MENT" or nonsteroidal. The nonsteroidal molecules are neither aromatized nor 5 alpha-reduced and may produce selective agonistic effects in some tissues (e.g. bone and muscle) but minimal agonistic or even antagonistic effects in other tissues such as prostate.

Calcimimetics:

Calcimimetics agents such as cinacalcet (Amgen's Sensipar) can be used to reduce osteoclast activity via PTH pathways. Calcimimetics increase sensitivity of calcium-sensing receptors on the cell surface of the parathyroid gland, which in turn reduces PTH secretion for a given level of calcium, which in turn reduces osteoclast activity and hence reduces extracellular calcium levels. Sensipar is currently used to treat secondary hyper parathyroidism (HPT) in patients with chronic kidney disease (CKD), associated with increases in parathyroid hormone (PTH) levels, which in turn stimulates osteoclastic activity, which in turn resulting in progressive bone loss and disordered mineral metabolism. In treatment of secondary hyper parathyroidism, Sensipar lowers levels of PTH, and hence lowers calcium and phosphorus in the blood, in order to prevent progressive bone disease and the systemic consequences of disordered mineral metabolism. Based on disclosures of present invention, cinacalcet could be used to lower PTH levels in order to lower baseline calcium levels, which in turn would lower the potential for nerve hypersensitization. Sensipar tablets for oral administration are available in strengths of 30 mg, 60 mg, and 90 mg of cinacalcet. Maximum plasma concentration (Cmax) is achieved in approximately 2 to 6 hours and cinacalcet concentrations decline in a biphasic fashion with a terminal half-life of 30 to 40 hours. Steady-state drug levels are achieved within 7 days.

Bisphosphonates:

Bisphosphonates can be used to inhibit osteoclastic activity and induce osteoclast apoptosis. Bisphosphonates include pamidronate, clodronate, zoledronate, etidronate, alendronate, risedronate, tiludronate, ibandronate, YH 529, EB-1053, incadronate, olpadronate, and neridronate. Newer generation bisphosphonate are more potent and have longer terminal half lives, while the older generation bisphosphonates typically have shorter functional half lives, making them better suited for short term applications. As a representative example, a 7.5 mg/kg dose of etidronate disodium (2 h infusion, ×3 days) was able to drop serum calcium levels by 2 mg/dl (from a baseline of 13.8 mg/dl) in 3 days and maintain efficacy for more than a week. Newer bisphosphonates such as zoledronic acid (Zometa) administer a 4 mg dose by 15 minute intravenous infusion and has an efficacy period of around 30 days. Pamidronate is commonly used to manage hypercalcemia and is given by IV infusion over 4 to 24 hours with doses or 30 mg if calcium levels are lower than 12 mg/dl, 60 mg if calcium levels are between 12 to 13.5 mg/dl, and 90 mg if calcium levels are above that level. Risedronate (Actonel from Procter & Gamble Pharmaceuticals) comes in a convenient oral form with tablets of 5 mg for daily administration, 35 mg for weekly, 75 mg on two consecutive days each month, or 150 mg once a month. Bisphosphonates could be used in a manner similar to calcimimetics described above.

RANK Receptor/RANK Ligand Inhibitors:

Any compounds that inhibit the two osteoclast promoter molecules (macrophage colony-stimulating factor and RANK ligand, that inhibit RANK receptor activation, or any compounds that facilitate, upregulate, or are functional analogues of osteoprotegerin (OPG), which blocks osteoclast formation by latching on to RANKL and blocking its function, can be used to reduce calcium levels. As an example, Amgen has filed denosumab, its fully human monoclonal antibody against RANK ligand, for treatment and prevention of postmenopausal osteoporosis in women and for prevention of bone loss in patients undergoing hormone ablation for either prostate or breast cancer. Based on disclosures of present invention, denosumab could be used for treatment of migraines and seizures, via its downregulation of osteoclast population density and hence reducing the release of calcium from bone into the extracellular fluid. Denosumab is administered at 60 mg., SC, ever 6 months.

Growth Hormone (GH) and Insulin Like Growth Factor 1 (IGF-1):

GH and IGF-1 are regulators of bone growth and bone mass. Although GH may act directly on skeletal cells, most of its effects are mediated by IGF-1, which is present in systemic circulation and is synthesized by peripheral tissues. The availability of IGF-1 is regulated by IGF binding proteins. IGF-1 enhances the differentiated function of the osteoblast in bone formation. Accordingly, GH and IGF-1 can be used to reduce extracellular calcium levels by moving calcium back into bone.

Bone Morphogenic Proteins (BMPs):

BMPs are a group of growth factors known for their ability to induce formation of bone. Of the seven BMPS originally discovered, six of them belong to the transforming growth factor (TGF) beta superfamily of proteins. Currently, at least 11 BMPs are known. Accordingly, BMPs could be used to reduce extracellular calcium levels by moving calcium back into bone. BMP-2 and BMP-7 play a key role in osteoblast differentiation and both have received FDA approval for human clinical uses. BMP-7 is available from Ortho Biotech, a subsidiary of Johnson & Johnson.

Vitamin D Inhibitors:

Downregulation of Vitamin D by avoidance of sunlight and dietary restrictions can be used to inhibit upregulation of osteoclast activity by inhibiting the VDR receptor pathways previously disclosed. Drugs that block calcitriol production could also be used and representative examples include ketoconazole, chloroquine, and hydroxychloroquine.

Phosphate:

Either oral or intravenous phosphate is effective in reducing serum calcium levels by causing a shift of calcium out of the extracellular fluid into bone and bone resorption is also inhibited (*Therapy of Renal Diseases and Related Disorders, Second Edition*, Kluwer Academic Publishers, 1991, page 96). Phosphate precipitates calcium to form calcium phosphate. Phosphate may also increase the efficacy of calcitonin therapy, since calcitonin increases renal clearance of phosphate, thereby attenuating its own effectiveness via this pathway when used alone (*Therapy of Renal Diseases and Related Disorders, Second Edition*, Kluwer Academic Publishers, 1991, page 97). Daily doses of 1-3 g of elemental phosphorus in three divided doses are typically used for management of hypercalcemia and therapy is contraindicated in renal failure and in the presence of serum phosphorous levels above 5 mg/dL. For purposes of present invention, doses would likely be started at the lower level of 1 g elemental phosphorus and escalated if necessary. Phosphate containing drugs can also be used to partially block intestinal calcium absorption (250-500 mg, four times daily) as insoluble calcium phosphate complexes are formed preventing absorption.

Other Compounds:

The above are only a few representative examples of materials that can be used to modulate extracellular calcium via modulation of the bone microenvironment and are presented only in order to fulfill the reduction to practice requirements of present invention and are not intended to limit the scope of present invention as any suitable compounds may be use instead of, or in combination with, the compounds disclosed above. Other endocrines known to modulate bone growth or bone resorption include, but are not limited to, fibroblast growth factor (FGF), platelet derived growth factor (PDGF), transforming growth factor (TGF) beta, and tumor necrosis factor (TNF). Saline hydration is often used to reduce calcium levels, either alone or with another therapy. Numerous other agents that could be used are also used or under development. Novartis is currently developing AAE581, a Cathepsin K inhibitor, which specifically inhibits the most potent enzyme involved in bone resorption, and accordingly could be used. As another example, gallium containing compounds can also be used to inhibit osteoclast activity. Another example is selective inhibitors of osteoclast vacuolar proton ATPase, which inhibit osteoclast activity. Another example is integrin receptor antagonists, which inhibit bone resorption by inhibiting integrin in osteoclasts, which is crucial for osteoclast cytoskeletal organization, cell migration, and cell polarization. Other examples would include PTH antibodies.

Adjuvants:

The above may also be used with adjuvants used under prior art to manage hypercalcemia, with doses adjusted accordingly to avoid hypocalcemia or other ill effects. Representative examples of prior art methods include, but are not limited to, expansion of extracellular fluid by administration of sodium solution (either IV or oral increased ingestion of water and salt or commercially available electrolyte solutions which typically contain sodium, potassium, and chloride), use of loop diuretics such as furosemide, bumetanide, ethacrynic acid, and torsemide that inhibit calcium reabsorption in the kidney and glucocorticoids such as prednisone. Excretion of calcium is achieved by inhibition of proximal tubular and loop sodium reabsorption via volume expansion (e.g. IV saline infusion 1-2 L for 1 hour) which results in a marked increase in sodium, calcium, and water delivery to the loop of Henle. A loop diuretic (e.g. furosemide) is used to block sodium transport in the loop, which results in a marked increase in urinary excretion of calcium, sodium, potassium, chloride, magnesium, and water so it is important to replace the other electrolytes continuously.

Calcium channel blockers may also be used and include over the counter compounds such as magnesium (e.g. 1 g/day). As previously disclosed, magnesium is a physiological calcium channel blocker, which would attenuate the inrush of calcium and attenuate that amount of neurotransmitter releases.

Assay Materials and Methods

Various prior art methods may be used to hone the doses and the timing of drug administrations relative to the symptoms. Any suitable prior art materials and methods for monitoring endocrine levels, osteoclast activity, or serum calcium concentration may be used or any suitable materials and methods for determining non bone resident calcium concentrations may be used.

Various materials and methods exist under prior art and representative examples of the above include, but are not limited to the following:

Monitoring estrogen levels would be useful for present invention and blood, saliva, and urine estradiol tests are available under prior art. Home saliva tests such as FemaleCheck provide a convenient method of tracking estrogen levels over the ovulation/menstruation cycle. Alternatively, estradiol hormone levels can be approximated for women that have regular menstrual cycles by use of an ovulation cycle diary. Likewise, any test for monitoring testosterone levels, active vitamin D levels (1,25 D and not 25 D), or prostaglandin levels would be useful in identifying, and facilitating management of, the underlying etiology under methods of present invention. Assays for monitoring any other endocrine levels that effect the bone microenvironment (e.g. GH, IGF-1, BMP, FGF, PDGF, TNF etc. . . . ) could also be employed to facilitate identification, characterization, and treatment of the factors contributing to the underlying etiology of the migraine or seizure condition.

Since methods of present invention modulate osteoclast, osteoblasts, or both in order to modulate calcium movement from bone, any suitable prior art assays and tests may be used to monitor progress or insure safety. Calcium blood levels may not accurately represent extracellular levels (e.g. blood concentrations are more tightly controlled and have the advantage of renal clearance, unlike extracellular levels). Monitoring serum levels is more relevant for safety purposes. Normal levels of serum calcium are in the range of 8.0 to 10.8 mg/dl (2.2 to 2.7 mmol/L) and the ionized calcium normal range is approximately 4 to 4.9 mg/dl and serum levels have more relevance for safety purposes by insuring the lower limits are not exceeded when using methods of present invention. Prior art methods may be used to observe efficacy of osteoclast downregulation over time by observing markers of osteoclast activity. Simple methods for determining osteoclast activity include measurement of various protein fragments and minerals released into the blood by the bone dissolving activity of osteoclasts (i.e. serum biochemical markers of bone resorption rates) such as calcium, deoxypyridinoline (DPD), or bone-specific alkaline phosphatase (BAP). During bone resorption, bone collagen is degraded, resulting in the release of calcium and several collagen cross links into the blood. Deoxypyridinoline (DPD) is involved in intermolecular and intramolecular cross linking and is specific to bone degradation. Monitoring serum concentrations of calcium (e.g. using s-cresolphthalein complexone; lyatron Co., Tokyo, Japan) or phosphate (e.g. enzyme assay; Kyowa Co., Tokyo Japan) are also available methods, as both are released into blood by bone resorption. Urinary excretion of pyridinoline and deoxypyridinoline, using Osteomark (NTX, Ostex) and Crosslaps (CTX, Osteometer) assays, are other methods available under prior art for monitoring bone resorption.

REDUCTION TO PRACTICE EXAMPLES

The guiding principle embodied in the examples under present invention is basically modulation of the bone microenvironment to alter extracellular calcium levels in a manner that functions to inhibit nerve and muscle hypersensitization in order to provide a novel treatment method for migraines and seizures.

Examples 1-3 are progressive, adding additional risk factors in each example for illustrative purposes. The discussion in each progressive example is generally limited to the new risk factors added for purposes of brevity and to keep the focus on the new risk factors and how they relate to then novel pathogenesis as disclosed in present invention as well as the novel treatments indicated based on same.

Example 4 is independent.

All examples assume the patient has been previously screened for known hypercalcemic conditions such as hyperparathyroidism, thyroid abnormalities, vitamin D metabolism abnormalities, kidney function abnormalities, calcium metabolism abnormalities etc. . . . and these conditions are not present.

Example 1

Puberty Related Seizures

A good representative example would be a 16 year old boy that started having seizures after the onset of puberty, with seizures often occurring later in the day. The patient has been on Depakote for the last two years, however, the drug is not working as well as well any more and the patient has started experiencing more frequent and more intense seizures.

Prior art treatment: As previously disclosed Depakote (Divalproex/valproate/valproic acid) increases brain concentrations of GABA (per the divalproex full prescribing information). GABA is the major inhibitory neurotransmitter in the body.

Present Invention Treatment: Because present invention is etiology focused, an understanding of the underlying etiology is presented first in order to understand the treatment methods.

Present Invention's Etiology: "The rise in plasma testosterone level at the start of male puberty begins as a result of sleep-related nocturnal gonadotropin surges, so that levels of plasma testosterone and LH are initially higher at night than during the day." (*Harrison's Principles of Internal Medicine*, McGraw-Hill, 15th edition, p. 2146). The nighttime surges continue, with daytime levels of testosterone eventually normalizing at the end of puberty. Based on disclosures of present invention, the puberty related testosterone oscillations would translate into oscillating cycles of calcium being reservoired in bone at night (osteoclast inhibition at night) followed by calcium being released from bone during the day (no daytime osteoclast inhibition), resulting in daytime calcium spikes. The elevated daytime extracellular calcium would in turn result in neuronal "hypersensitization" via 1) neuronal membrane depolarization, 2) upregulated neurotransmitter release at synapses, and 3) PTP mechanisms, as previously disclosed and muscular "hypersensitization" via 1) enhanced neurotransmitter release at the neuromuscular junction and 2) directly enhanced muscle contractility via the enhanced inrush of $Ca^{2+}$ into the sarcoplasmic reticulum, enhanced tropomyosin block removal, enhanced actin-myosin cross-bridging. The neuronal hypersensitization would be particularly dangerous to people with low seizure thresholds. The increased muscle contractility would contribute to the severity of the involuntary muscle contractions experienced during the seizure.

The other event that occurs through the roughly 6 years of puberty is that testes grow from around 2 ml in volume to 12-25 ml in volume, with plasma testosterone levels rising sharply, around fifty fold, from 0.1 ng/ml (0.05-.2 ng/ml) in prepubertal boys to around 5 ng/ml (3-10 ng/ml) by the end of puberty. Under disclosures of present invention, this would result for progressively larger testosterone related calcium swings. Larger swings could overwhelm the ability of Depakote to prevent the seizures. Large swings in either direction have the potential to induce seizures, as previously disclosed (i.e. in hypercalcemia, EEG changes appear when serum calcium levels reach 13 mg/dl and above 16 mg/dl grand mal attacks occur and in hypocalcemia, epileptic manifestations develop at calcium levels of 5-6 mg/dl). Since the patient experiences daytime seizures, excessive release of calcium into the extracellular fluid would be the cause of the seizures under pathogenesis of present invention.

Present Invention Treatment: The focus of present invention would be to modulate the daytime bone microenvironment activity levels to attenuate the level of calcium being released from bone.

The patient is instructed to limit calcium and vitamin D intake and to avoid sunlight (to prevent exacerbating the daytime calcium spike).

Numerous compositions and methods may be used to inhibit daytime osteoclast activity. They may be used as stand alone agent, concurrent with one or more other osteoclast inhibitors, and concurrent with Depakote or other anti seizure medications that attenuate nerve transmission as previously disclosed. Some examples of treatment methods of present invention:

Testosterone: Normal testosterone levels range from 300 ng/ml to 1,000 ng/ml at the end of puberty, and are more homogeneously distributed between the night and day at the end of puberty. For the patient going through puberty and experiencing daytime drops in testosterone, daytime testosterone administration may be used to maintain more even levels of testosterone over the 24 hour period. As an example, WatsonPharma's Androderm transdermal 2.5 mg testosterone patch, when applied to the upper arm, raised testosterone levels from a baseline of 81 ng/dl to 308 ng/dl in 3 hours, 468 in 6 hours, 534 in 9 hours and 527 in 12 hours. The elimination half life of the testosterone is 71 minutes. Accordingly, the patch could be administered upon waking, and removed prior to bedtime. This would keep testosterone levels elevated during the day, and keep calcium from being released into extracellular fluid where it would hypersensitize nerves and pose a seizure risk. Alternatively, a lower or higher dose may be used depending on the individuals nightly testosterone levels and depending on where they are in the puberty progression timeline. A lower dose could also be used (e.g. half patch, impermeable insert under half the patch, or just a dose lower then 2.5 mg per patch) or the patch could be removed for part of the time then replaced. If a higher dose is desired, the Androderm patch also comes in a 5 mg dose. Alternatively, administration of hormones that upregulate indigenous production of testosterone, such as luteinizing hormone or gonadotropin/luteinizing hormone releasing hormone, can be substituted, as previously disclosed.

Calcitonin: After the patient is screened for calcitonin allergies in accordance with the manufacturers prescribing information, the patient could be prescribed nasal calcitonin-salmon spray (Miacalcin from Novartis and Fortical from Upsher-Smith) and instructed to administer a spray in each nostril (i.e. 200 IU×2=400 IU) upon waking. The patient is instructed to administer 400 IU (or 200 IU) every 6-8 hours. Rationale for Calcitonin: Having previously disclosed the etiology as upregulated osteoclast activity (caused by the daytime drop in testosterone levels) the administration of the more potent, exogenous salmon-calcitonin is intended to inhibit/reduce osteoclast mediated release of calcium during the daytime.

Phosphate: Either oral or intravenous phosphate is effective in reducing serum calcium levels by causing a shift of calcium out of the extracellular fluid into bone and bone resorption is also inhibited. Phosphate precipitates calcium to form calcium phosphate. Phosphate may also increase the efficacy of calcitonin therapy, since calcitonin increases renal clearance of phosphate, thereby attenuating its own effectiveness via this pathway when used alone. Daily doses of 1-3 g of elemental phosphorus in three divided doses are typically used for management of hypercalcemia and therapy is contraindicated in renal failure and in the presence of serum phosphorous levels above 5 mg/dL. For purposes of present invention, doses would likely be started at the lower level of 1 g elemental phosphorus and escalated if necessary.

Magnesium: Magnesium supplements could be incorporated into the regimen. The patient would ingest a 400 mg dose of magnesium upon waking and 400 mg after lunch. Magnesium is a physiological calcium channel blocker and would function to attenuate the effects of daytime calcium spike.

The above are only a few representative examples of compositions that could be used under present invention are not intend to limit the scope of the invention. Innumerable variants, combinations, and substitutions of doses and schedules are possible. The above representative examples are presented only to fulfill the reduction to practice requirement of present invention. The scope of specifications, and the related claims, is intended to cover modulation of the bone microenvironment in a manner that inhibits endocrine modulated release of calcium from bone into extracellular fluid in order to prevent hypersensitization of nerves and increased risk for seizure.

It should also be noted that even if the underlying etiology of the seizure were something else, the methods of present invention would still work, because as previously disclosed, dropping extracellular calcium levels desensitizes nerves.

Summary of Novelty and Unobviousness Over Prior Art: Use of Depakote is typical of prior art's approach of administering compounds that inhibit nerve transmission, versus present invention's approach of modulating the bone microenvironment to prevent the condition that hypersensitized the nerves in the first place. Depakote's activation of both GABA receptor types A and B would work to counteract the Ca2+ nerve hypersensitization. The $GABA_A$ related hyperpolarization would work to counteract the Ca2+ membrane depolarization. The $GABA_B$ related voltage gated calcium channel inhibition and downregulation of presynaptic neurotransmitter release would work to counteract the upregulation of presynaptic neurotransmitter release from the larger Ca2+ inrush through the voltage gated calcium channels under pathogenesis of present invention. Methods of present invention focus on inhibiting the underlying etiology, or earliest event, which means inhibiting the release of Ca2+ in the first place. Methods of present invention can be used concurrent with prior art's Depakote for dual action protection. In the above example, it would also help to Depakote keep working in order to keep progressive increases in testosterone levels from overwhelming Depakote's ability to prevent seizures.

Present invention's approach is unobvious over prior art in that prior art does not know the underlying etiology of most seizures, including that in the example above. Hence it would not be obvious to one skilled in the art to address the underlying etiology, since they don't know what the underlying etiology is.

Example 2

Puberty Related Seizures with Escalated Risk

The 16 year old boy of Example 1 is used in this example, except with additional risk factors added. The patient started having seizures after the onset of puberty, with seizures typically occurring later in the day. The patient has been on Depakote for the last two years, however, the drug is not working as well as well any more and the patient has started experiencing more frequent and more intense seizures.

The patient's family is planning a month long trip to a tropical island and plan to spend much time on the beach and fishing in the ocean. The patient is fair skinned. The patient's calcium levels are in the upper part of the normal range at 10.5 mg/dl (8.5-10.8 mg/dl=normal range).

Prior art Treatment: Depakote is the prior art treatment use in the example. Without understanding the underlying etiology as presented in present invention, prior would not understand the grave danger facing the boy.

Present Invention's Etiology: Under disclosures of present invention, the patient is now facing 3 potential sources of abrupt escalations in extracellular calcium levels, via endocrine—bone microenvironment mediated events.
1) Testosterone—The nightly testosterone surges related to puberty, followed by the daytime drops in testosterone, are the first source of daytime extracellular calcium spikes as discussed in detail in Example 1.
2) Vitamin D—The beach and ocean related exposure to sun contributes a second potential calcium spike. As previously disclosed, exposure to sunlight (UVB) would have a material effect on vitamin D levels, and hence extracellular calcium levels. Full body exposure to UVB for 20 minutes in midday summer sun, in fair skinned people, can result in 10,000 IU of biologically active 1,25 vitamin D being synthesized by the skin (25 times the recommended daily allowance of 400 IU). The effectively unregulated production of active 1,25 D by the skin would boost $Ca^{2+}$ levels by the three pathways previously disclosed (i.e. increased release of calcium from bone, increased reabsorption of calcium by the kidneys, and increased absorption of calcium from the intestines) and the biological effect would last for a period of time commensurate with the amount of 1,25 D synthesized and its half life of 3-6 hours.
3) Prostaglandins—If the patient gets any sunburn, prostaglandins become the third contributor to a calcium spike. Prostaglandins are released in response to cell destruction. As previously disclosed, increases in prostaglandin levels would result in increased extracellular calcium levels as prostaglandins exhibit PTH-like (parathyroid hormone) effects that result in calcium mobilization from the bone. The prostaglandin induced bone resorption would increase extracellular calcium levels.

All three of the endocrine oscillations listed above would result in a sharp rise in extracellular calcium levels, which would in turn follow the same pathogenesis pathways previously disclosed, namely neuronal "hypersensitization" via 1) neuronal membrane depolarization, 2) upregulated neurotransmitter release at synapses, and 3) PTP mechanisms and muscular "hypersensitization" via 1) enhanced neurotransmitter release at the neuromuscular junction and 2) directly enhanced muscle contractility via the enhanced inrush of $Ca^{2+}$ into the sarcoplasmic reticulum, enhanced tropomyosin block removal, enhanced actin-myosin cross-bridging. This increases the risk related to the potential for seizures, the severity of seizures, and the severity of the seizure associated muscle contractions.

Present Invention Treatment:

Because of the prolonged threat from the triple $Ca^{2+}$ spike risk over the month long vacation, the treatments under present invention are ratcheted up accordingly.

Calcimimetics: Calcimimetics agents such as cinacalcet (Amgen's Sensipar) can be used to reduce osteoclast activity via PTH pathways. Calcimimetics increase sensitivity of calcium-sensing receptors on the cell surface of the parathyroid gland, which in turn reduces PTH secretion for a given level of calcium, which in turn reduces osteoclast activity and hence reduces extracellular calcium levels. Cinacalcet could be used to lower PTH levels in order to lower baseline calcium levels, which in turn would lower the potential for nerve hypersensitization. Sensipar tablets for oral administration are available in strengths of 30 mg, 60 mg, and 90 mg of cinacalcet. Maximum plasma concentration (Cmax) is achieved in approximately 2 to 6 hours and cinacalcet concentrations decline in a biphasic fashion with a terminal half-life of 30 to 40 hours. Steady-state drug levels are achieved within 7 days. For purposes of present invention, patient would be started at the lowest, 30 mg dose, or as allowed for by the individual patient's calcium levels.

RANK Receptor/RANK Ligand Inhibitors: As an example, Amgen's human monoclonal antibody against RANK ligand, denosumab, could be used for its ability to downregulate osteoclast population density and hence reduce the potential for release of large amounts of calcium from bone into the extracellular fluid. Denosumab is administered at 60 mg., SC, every 6 months.

Bisphosphonates: Bisphosphonates can be used to inhibit osteoclastic activity and induce osteoclast apoptosis in order to reduce the intensity of any osteoclast mediated calcium spike. As a representative example, a 5 mg daily tablet of risedronate (Actonel from Procter & Gamble) would be administered 30 minutes before the first food or drink of the day. Bisphosphonates would be used in a manner similar to calcimimetics described above.

The testosterone level modulating treatments of Example 1 should also be used. Other treatment used in Example 1 may also be integrated.

Testosterone: For the patient going through puberty and experiencing daytime drops in testosterone, daytime testosterone administration may be used to maintain more even levels of testosterone over the 24 hour period. The WatsonPharma's Androderm transdermal 2.5 mg testosterone patch could be used as discussed in Example 1.

Calcitonin: Nasal calcitonin-salmon spray (Miacalcin from Novartis and Fortical from Upsher-Smith) could also be used as in Example 1. Alternatively, the preferred embodiment would reserve use of the calcitonin for use in the event a second or third risk factor materialized. As an example, if the patient was exposed to full body sun from a beach or fishing experience, they would administer a spray in each nostril (i.e. 200 IU×2=400 IU) at the time of the event and 6-8 hours thereafter. Rationale: The extra anti-calcium spike protection is designed to protect from the anticipated Vitamin D spike form sun exposure, which translates into a extracellular calcium spike as previously disclosed.

Phosphate: Either oral or intravenous phosphate could be used as in Example 1. Alternatively, phosphate could be administered prior to, during, or immediately after a sun exposure event as in the calcitonin example above.

Magnesium: Magnesium supplements should be incorporated into the regimen as in Example 1. The patient would ingest a 400 mg dose of magnesium upon waking and 400 mg after lunch. Magnesium is a physiological calcium channel blocker and would function to attenuate the effects of daytime calcium spike.

Additionally,

Vitamin D blockers: If sun exposure without sunburn is involved, vitamin D blockers/inactivators may also be used (e.g. ketoconazole, chloroquine, hydroxychloroquine, as previously disclosed).

NSAIDs: If a sunburn is involved, prostaglandin inhibitors, such as NSAIDs (e.g. Aleve), would be used to reduce prostaglandin levels, and hence reduce the elevated extracellular calcium levels from this endocrine source.

The above are only a few representative examples of compositions that could be used under present invention are not intend to limit the scope of the invention. Innumerable variants, combinations, and substitutions of doses and schedules are possible. The above representative examples are presented only to fulfill the reduction to practice requirement of present invention. The scope of specifications, and the related claims, is intended to cover modulation of the bone microenvironment in a manner that inhibits endocrine modulated release of calcium from bone into extracellular fluid in order to prevent hypersensitization of nerves and increased risk for seizure.

Summary of Novelty and Unobviousness Over Prior Art: Use of Depakote is typical of prior art's approach of administering compounds that inhibit nerve transmission, versus present invention's approach of modulating the bone microenvironment to prevent the condition that hypersensitized the nerves in the first place. The absence of additional precautions by prior art, in light of elevated risks presented in the example above, are related to prior art's lack of knowledge about what the etiology of most seizures is.

Present invention's approach is unobvious over prior art in that prior art does not know the underlying etiology of most seizures, including that in the example above. Hence it would not be obvious to one skilled in the art to address the underlying etiology, since they don't know what the underlying etiology is.

Example 3

Puberty Related Seizures with Extreme Risk

The patient of Example 2 is also taking retinoic acid derivatives (Vitamin A) for acne and is on lithium therapy for mood stabilization.

The patient now has five risk factors, putting him in extreme seizure danger of extremely high endocrine—bone microenvironment modulated calcium spikes, which as disclosed under pathogenesis of present invention pose extreme risk of nerve hypersensitization and seizures.

The endocrine modulated, bone microenvironment calcium release, risks are:
1) Retinoid Therapy: Retinoids (Vitamin A derivatives) increase osteoclast bone resorption and patients taking retinoic acid derivatives for treatment of acne often experience elevated calcium levels
2) Lithium Therapy: Patients treated with lithium commonly develop mild hypercalcemia. It appears that lithium increases the set point for PTH suppression by calcium.
3) Testosterone: As described in Example 1.
4) Sun/Vitamin D: As described in Example 2.
5) Sun/Sunburn/Prostaglandins: As described in Example 2.

Present Invention Treatment: The patient is taken off of lithium and retinoid therapy. Lithium can be replaced with a mood stabilizing drug that does not have the potential for elevating calcium levels. The retinoid therapy is replaced with a topical, non retinoid based acne therapy. The patient is treated with compositions an methods as described in Example 2 for the daily testosterone drops and sun exposure risks.

Novelty over Prior Art: The purpose of the example is to show that seizure patients taking any drugs would have to have them reviewed in light of their potential for modulating the bone microenvironment and calcium levels and hence increasing seizure potential.

Example 4

Premenstrual/Menstrual Related Seizures

The patient used in this example is one of the 78% of women with refractory epilepsy that reported most of their seizures occurred near the time of and were exacerbated by menstruation (Duncan S et. al., "*How common is catamenial epilepsy*", *Epilepsia*, 1993 September-October,; 34(5):827-31). The patient's calcium levels are in the upper half of the normal range for purposes of this example.

Prior art Treatment: Numerous prior art anti-seizures medications exist that function by inhibiting nerve transmission, as previously disclosed.

Present Invention's Etiology: Under pathogenesis disclosures of present invention, two endocrine related events would be occurring to cause the nerve hypersensitization:

Estrogen—As previously disclosed, menstruation involves a precipitous drop in estrogen levels (FIG. 1 day 28, and FIG. 1 days 1-9) with the most pronounced elevation in extracellular calcium levels from bone resorption starting on day 28 (as the estrogen "brakes" on osteoclast activity are removed), as previously disclosed. The calcium that had been "reservoired" in bone for the 3 weeks prior to the start of menstruation (FIG. 2) is now poised to be released over the next several days.

Prostaglandins—As previously disclosed, prostaglandins are also released during menstruation due to destruction of the endometrial cells, which also release calcium from bone. This would further contribute to raising extracellular calcium levels.

The elevated extracellular calcium levels from both the drop in estrogen and rise in prostaglandins would in turn result in neuronal "hypersensitization" via 1) neuronal membrane depolarization, 2) upregulated neurotransmitter release at synapses, and 3) PTP mechanisms and muscular "hypersensitization" via 1) enhanced neurotransmitter release at the neuromuscular junction and 2) directly enhanced muscle contractility via the enhanced inrush of $Ca^{2+}$ into the sarcoplasmic reticulum, enhanced tropomyosin block removal, enhanced actin-myosin cross-bridging, as previously disclosed. This is particularly important to people with low seizure thresholds. This increases the potential for seizures, the severity of the seizures, and severity of seizure associated muscle contractions.

As methods of present invention target the bone microenvironment to prevent release of the calcium, they would directly counteract the underlying etiology to prevent the hypersensitization event.

Present Invention's Treatment:

SERM: In the preferred embodiment of present invention, a SERM such as raloxifene is used, which effectively replaces estrogen's functions in the bone microenvironment, without commensurate effect on uterine or breast cells. Raloxifene inhibits osteoclast activity, which in turn inhibits the rise of extraceHular calcium levels. As a representative example, the patient is initially prescribed a 0.5 mg/kg oral daily dose of Raloxifene hydrochloride to be taken two days prior to the start of menstruation and continued until the end of menstruation. A single dose as prescribed above, would provide a maximum plasma concentration of around 0.25 ng/dl with a serum half life of around 28 hours. If seizures are still experienced, the dose could be escalated. Alternatively, any other suitable dose or schedule may be used as appropriate. As a representative example, a 1 mg/kg daily dose of Raloxifene hydrochloride would boost blood levels to 0.5 ng/dl, which is higher than the highest estrogen levels achieved during the ovulation cycle (FIG. 2), and would provide a very high level of osteoclast inhibition and hence calcium retention. Increasing the duration of the regimen (e.g. starting 5 or 6 days prior to start of menstruation, or when estrogen levels first start dropping as shown in FIG. 2) should also result in an increased amount of the "reservoired" calcium being retained in bone. This may have advantages for reducing osteoporosis risks later in life. As previously disclosed, women peak at 5% less bone density than men, and a regimen like this may level the playing field for osteoporosis risk, while simultaneously reducing seizure risk and severity. The selectivity of raloxifene's effect to osteoclasts, without uterine effects that could potential interfere with menstrual related uterine events, provide a method to effectively maintain estrogen's "brakes" on osteoclasts, through the drop in indigenous estrogen levels. The related extracellular calcium level elevations would thus be eliminated, which in turn would prevent nerve and muscle hypersensitization, as previously disclosed.

SERM/Estradiol: If the patient is on birth control, which is basically 3 weeks of estrogen followed by 1 week of sugar pills, the SERM raloxifene could be substituted for the sugar pills. Alternatively, low levels of estrogen could be substituted for one or more of the sugar pills, with the goal of keeping the serum levels around 0.1 ng/ml, without the sharp transition drop, and without the potential for interfering with progression of menstruation. Alternatively, an estrogen patch may be used. As previously disclosed a 0.10 mg estradiol transdermal patch results in an escalation of serum estrogen levels by around 0.1 ng/ml, which is around the baseline estrogen level during menstruation.

NSAIDs: Nonsteroidal Anti-Inflammatory Drugs could be used concurrently to lower prostaglandin levels, the other contributor to bone microenvironment modulated calcium release. Although NSAIDs are used under prior art for migraines, based on disclosures of present invention, they would have relevance to seizures, when the seizures are caused, in whole or in part, by elevations in prostaglandin levels. Preferred embodiment of present invention uses aleve, however any suitable NSAID could be substituted, including over the counter NSAIDs such as excedrin migraine, vioxx, celebrex, advil, motrin IB, nuprin, actron, orudis KT, aspirin (bayer, bufferin, ecotrin), and tylenol. NSAIDs used for preventative therapy could also include cataflam, lodine, ansaid, genpril, haltran, ibifon, ibren, ibu, ibuprin, ibuprohm, ibu-tab, medipren, motrin, q-profen, toradol, meclomen, and anaprox.

Magnesium: With a large percentage of women typically being magnesium deficient, magnesium supplements could be incorporated as part of the regimen, and absolutely should be incorporated for women with magnesium deficiencies. The patients would ingest a 200 mg -400 mg dose of magnesium, twice daily (any other suitable amount or schedule may be substituted). Magnesium is a physiological calcium channel blocker and would function to attenuate the effects of any calcium spike.

Additional treatments may be included or substituted as indicated.

Calcitonin: After patient is screened for calcitonin allergies in accordance with the manufacturers prescribing information, the patient could be prescribed nasal calcitonin-salmon spray (Miacalcin from Novartis and Fortical from Upsher-Smith) and instructed to administer between 200 IU -400 IU every 6-8 hours. The calcitonin is used to inhibit/reduce osteoclast mediated release of calcium during the menstruation period.

Phosphate: Either oral or intravenous phosphate is effective in reducing serum calcium levels by causing a shift of calcium out of the extracellular fluid into bone and bone resorption is also inhibited. Phosphate precipitates calcium to form calcium phosphate. Phosphate may also increase the efficacy of calcitonin therapy, since calcitonin increases renal clearance of phosphate, thereby attenuating its own effectiveness via this pathway when used alone. Phosphate containing drugs can also be used to partially block intestinal calcium absorption (250-500 mg, four times daily) as insoluble calcium phosphate complexes are formed preventing absorption. Phosphate therapy is contraindicated in renal failure and in the presence of serum phosphorous levels above 5 mg/dL.

Heavier duty treatments could also be used and include:

Calcimimetics: Calcimimetics agents such as cinacalcet (Amgen's Sensipar) can be used to reduce osteoclast activity via PTH pathways. Calcimimetics increase sensitivity of calcium-sensing receptors on the cell surface of the parathyroid gland, which in turn reduces PTH secretion for a given level of calcium, which in turn reduces osteoclast activity and hence reduces extracellular calcium levels. Cinacalcet could be used to lower PTH levels in order to lower baseline calcium levels, which in turn would lower the potential for nerve hypersensitization. Sensipar tablets for oral administration are available in strengths of 30 mg, 60 mg, and 90 mg of cinacalcet. Maximum plasma concentration (Cmax) is achieved in approximately 2 to 6 hours and cinacalcet concentrations decline in a biphasic fashion with a terminal half-life of 30 to 40 hours. Steady-state drug levels are achieved within 7 days. For purposes of present invention, patient would be started at the lowest, 30 mg dose, or as allowed for by the individual patient's calcium levels.

RANK Receptor/RANK Ligand Inhibitors: As an example, Amgen's human monoclonal antibody against RANK ligand, denosumab, could be used for its ability to downregulate osteoclast population density and hence reduce the potential for release of large amounts of calcium from bone into the extracellular fluid. Denosumab is administered at 60 mg., SC, every 6 months.

Bisphosphonates: Bisphosphonates can be used to inhibit osteoclastic activity and induce osteoclast apoptosis in order to reduce the intensity of any osteoclast mediated calcium spike. As a representative example, a 5 mg daily tablet of risedronate (Actonel from Procter & Gamble) would be administered 30 minutes before the first food or drink of the day. The schedule would start a few days before start of menstruation and could continue until up to 10 days after the start of menstruation. Bisphosphonates would be used in a manner similar to calcimimetics described above.

Scope of Invention/Alternate Examples

As methods of present invention target bone microenvironment to prevent release of the calcium, they would provide the most benefit in cases where the seizures were dependent, in whole or in part, on elevations in calcium levels, as the compositions and methods disclosed in Examples 1-4 above would directly counteract the underlying etiology of escalating calcium release from bone and hence prevent the subsequent hypersensitization event from ever happening.

However, the scope of the invention is not intended to be limited to only seizures that involve elevations in extracellular calcium levels as part of their etiology. It is not even necessary for the underlying etiology to be related to elevations in extracellular calcium levels for methods of present invention to provide therapeutic benefit. Seizures with other known etiologies would also benefit from neuronal "desensitization". This can best be explained by following the pathways previously presented in reverse, showing how decreasing extracellular calcium would provide therapeutic benefit, even if elevations in extracellular calcium levels was not the dominant underlying etiology. Lowering extracellular calcium levels would result in "desensitization" of nerves via 1) neuronal membrane hyperpolarization, 2) downregulated neurotransmitter release at synapses, and "desensitization" of muscles via 1) reduced neurotransmitter release at the neuromuscular junction and 2) reduced muscle contractility via the reduced inrush of $Ca^{2+}$ into the sarcoplasmic reticulum, reduced tropomyosin block removal, reduced actin-myosin cross-bridging, as previously disclosed. This would be therapeutically beneficial to all people with low seizure thresholds.

The above representative examples have innumerable variants and are not intended to limit the scope of the invention, but only to provide a few efficacious and safe examples to fulfill the reduction to practice requirement of instant application. The scope of the invention is intended to encompass the following:
1) a method of treating seizures by modulating the bone microenvironment to inhibit or attenuate the release of calcium from bone into extracellular fluid or
2) a method of treating seizures by modulating the bone microenvironment to promote the removal of calcium from extracellular fluid and storing it in bone The doses, drugs, routes of administration, and adjuvants used in the above representative examples have innumerable variants and are not intended to limit the scope of the invention. The representative examples are not intended to suggest optimal doses, drugs, routes of administration or regimens but only to provide a few representative examples of efficacious and safe treatments to fulfill the reduction to practice requirement of this application. Optimal doses, drugs, routes of administration, and regimens would be further honed as is customary under prior art in controlled human clinical trials.

For purposes of present invention and its related claims, calcitonin is defined as calcitonin, calcitonin agonists, calcitonin analogs, or any molecule that exhibits the biological function of calcitonin or activates pathways normally activated by calcitonin, such as osteoclast activity downregulation, increased renal reabsorption of calcium, or increased absorption of calcium from the gastrointestinal tract. Representative examples of calcitonin include, but are not limited to, human calcitonin, salmon calcitonin, and synthetic salmon calcitonin such as Fortical from Upsher-Smith and Miacalcin form Novartis.

For purposes of present invention and its related claims, anti-osteoclast SERM (selective estrogen receptor modulator) is defined as any molecule that activates pathways normally activated by estrogen, as they relate to osteoclast population downregulation or osteoclast activity downregulation and downregulation of extracellular concentration of calcium. Representative examples of anti-osteoclast SERMs that downregulate osteoclasts include, but are not limited to, raloxifene and tamoxifen.

For purposes of present invention and its related claims, when the word "or" is used, it is used to mean "either or both".

The scope of invention is intended to encompass the use of any anti-osteoclast compound(s) or any pro-osteoblast compound, and not limited to the few representative examples presented. Anti-osteoclast compounds are hereby defined as any substance, either currently known or to be discovered or developed in the future, that inhibit osteoclast related release of calcium from the bone. Anti-osteoblast compounds are hereby defined as any substance, either currently known or to be discovered or developed in the future, that promote osteoblast related storage of calcium in bone.

The scope of invention is also intended to encompass the use of any adjuvant compounds or methods that function to counteract any aspects of the underlying etiology, or downstream events, as disclosed by present application or that could reasonably be anticipated by one skilled in the art.

Summary of Novelty and Unobviousness

Prior art has admitted its inability to elucidate the underlying etiology/pathogenesis related to the majority of recurring seizures.

Present invention has finally elucidated the underlying etiology/pathogenesis of a portion of these previously unexplained seizures, and accordingly has provided novel, powerful etiology based treatment methods.

Present invention not only outlined the etiology and subsequent pathways, but corroborated them by explaining the numerous prior art clinical observations in light of the new etiology/pathophysiology, as well as reviewing prior art drugs as to why they would be expected to work under pathogenesis of present invention. In addition to having a solid scientific MOA basis, the pathogenesis of present invention is also consistent with all of the prior art observations and data.

Prior art seizure treatments are focused on impairing neuronal transmission (typically of some subset of nerves). In contrast, bone microenvironment modulation methods of present invention (i.e. osteoclast inhibition or osteoblast upregulation) are not a prescribed seizure treatment under prior art, making a prima facie case for unobviousness.

Because the protocols of present invention are based on a novel etiology/pathogenesis that is not known (and not obvious) to prior art, the treatments presented herein would also have been unobvious to prior art practitioners.

Utility

Having elucidated the underlying etiology and subsequent pathways in this application (i.e. from endocrine to bone to nerve/brain), present invention targets the earliest possible events (i.e. in the bone) in order to prevent the subsequent systemic hypersensitization events that result. In contrast, prior art treatments focus on fairly downstream events (e.g. impairing nerve transmission), in large part because prior art had not identified the underlying etiology and was left with treating symptoms/observations.

Accordingly, present invention will provide great utility by targeting the earliest events in these conditions, which should provide the greatest benefit. Alternatively, combining the etiology based treatments of present invention, with prior art symptoms based treatments as adjuvants, would also greatly improve the potential for seizure relief in patients.

I claim:

1. A method of treating seizures consisting of administrating, to a patient in need thereof, a therapeutically effective amount of raloxifene in a dosage form to inhibit release of calcium from bone.

* * * * *